US009603979B2

(12) United States Patent
Ghigo et al.

(10) Patent No.: US 9,603,979 B2
(45) Date of Patent: Mar. 28, 2017

(54) USE OF BACTERIAL POLYSACCHARIDES FOR BIOFILM INHIBITION

(71) Applicants: Jean-Marc Ghigo, Fonteney-Aux-Roses (FR); Jaione Valle, Paris (FR); Sandra Da Re, Limonges (FR)

(72) Inventors: Jean-Marc Ghigo, Fonteney-Aux-Roses (FR); Jaione Valle, Paris (FR); Sandra Da Re, Limonges (FR)

(73) Assignees: INSTITUT PASTEUR, Paris (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 15/002,315

(22) Filed: Jan. 20, 2016

(65) Prior Publication Data

US 2016/0235894 A1 Aug. 18, 2016

Related U.S. Application Data

(60) Division of application No. 14/842,766, filed on Sep. 1, 2015, which is a continuation of application No. 13/482,468, filed on May 29, 2012, now abandoned, which is a continuation of application No. 12/307,045, filed as application No. PCT/IB2007/002875 on Jun. 25, 2007, now abandoned.

(30) Foreign Application Priority Data

Jun. 30, 2006 (EP) .................... 06291080

(51) Int. Cl.
| A61K 35/74 | (2015.01) |
| A61L 31/10 | (2006.01) |
| A61K 31/715 | (2006.01) |
| A61L 2/232 | (2006.01) |
| A01N 25/08 | (2006.01) |
| A01N 43/16 | (2006.01) |
| A61L 29/08 | (2006.01) |
| A61L 29/14 | (2006.01) |
| A61L 31/14 | (2006.01) |
| A01N 63/02 | (2006.01) |
| A61L 2/18 | (2006.01) |
| B05D 1/18 | (2006.01) |

(52) U.S. Cl.
CPC ............ A61L 31/10 (2013.01); A01N 25/08 (2013.01); A01N 43/16 (2013.01); A01N 63/02 (2013.01); A61K 31/715 (2013.01); A61L 2/18 (2013.01); A61L 2/232 (2013.01); A61L 29/085 (2013.01); A61L 29/14 (2013.01); A61L 31/14 (2013.01); B05D 1/18 (2013.01); A61L 2300/232 (2013.01); A61L 2300/404 (2013.01); A61L 2420/00 (2013.01); A61L 2420/02 (2013.01)

(58) Field of Classification Search
USPC ......................................................... 514/23
IPC ...................................................... A61K 35/74
See application file for complete search history.

(56) References Cited

U.S. PATENT DOCUMENTS

| 4,711,779 A | 12/1987 | Porro et al. |
| 4,727,136 A | 2/1988 | Jennings et al. |
| 5,071,969 A | 12/1991 | Van Boeckel et al. |
| 5,384,398 A | 1/1995 | Lormeau et al. |
| 5,902,586 A | 5/1999 | Jennings et al. |
| 6,248,570 B1 | 6/2001 | Michon et al. |
| 2003/0165870 A1 | 9/2003 | Blattner et al. |
| 2003/0180316 A1 | 9/2003 | Boutriau et al. |
| 2004/0132143 A1* | 7/2004 | DeAngelis ............ A61K 47/36 435/89 |
| 2005/0106184 A1 | 5/2005 | Franks et al. |
| 2006/0188966 A1* | 8/2006 | DeAngelis ............ A61K 47/36 435/85 |
| 2008/0032349 A1 | 2/2008 | Viskov et al. |
| 2009/0208533 A1 | 8/2009 | Stephens et al. |
| 2009/0318382 A1* | 12/2009 | Ghigo .................... A61L 2/232 514/54 |
| 2010/0015212 A1 | 1/2010 | Adu-Bobie et al. |
| 2010/0136027 A1 | 6/2010 | Kim et al. |
| 2012/0308632 A1* | 12/2012 | Ghigo .................... A61L 2/232 424/411 |

FOREIGN PATENT DOCUMENTS

| EP | 0208375 A1 | 1/1987 |
| EP | 0333243 A2 | 9/1989 |
| JP | 5-505392 | 8/1993 |
| JP | 5-271305 | 10/1993 |
| JP | 2007-514817 A | 6/2007 |
| JP | 2008-512105 A | 4/2008 |
| JP | 2008-517617 A | 5/2008 |

(Continued)

OTHER PUBLICATIONS

Wyle, et al., J. Infect. Dis., vol. 136, No. 5, pp. 514-522 (1972).
Office Action dated Dec. 21, 2010 issued in European Patent Application No. 06 291 080.7.
Office Action dated Mar. 6, 2012 issued in Japanese Patent Application No. 2009-517481 (English translation only).
Chris Whitfield—"Biosynthesis and Assembly of Capsular Polysaccharides in *Escherichia coli*", Annu. Rev. Biochem. 2006, 75, pp. 39-68.

(Continued)

Primary Examiner — Chris R Tate
(74) Attorney, Agent, or Firm — Arrigo, Lee & Guttman LLP

(57) ABSTRACT

A method comprises preventing or inhibiting bacterial adhesion and/or bacterial biofilm development by treating a substrate with a composition of a soluble group II capsular polysaccharide obtained from a bacterial strain.

18 Claims, 16 Drawing Sheets

(56) References Cited

FOREIGN PATENT DOCUMENTS

| WO | 91/08772 A1 | 6/1991 |
|---|---|---|
| WO | 0102597 A1 | 1/2001 |
| WO | 2005/058976 A2 | 6/2005 |
| WO | 2006/030099 A1 | 3/2006 |
| WO | 2006/046143 A2 | 5/2006 |

OTHER PUBLICATIONS

Bahrani-Mougeot et al. Mol. Microbiol. 2002. vol. 45, No. 2, pp. 1079-1093, Jun. 28, 2016.
Roberts, I. Annu. Rev. Microbiol. 1996. vol. 50, pp. 285-315.
Whitfiled et al. Carbohydrate Res. 2003. vol. 338, pp. 2491-2502.
Welch, R. A. et al., "Extensive mosaic structure revealed by the complete genome sequence of uropathogenic *Escherichia coli*", PNAS, vol. 99, No, 26, pp. 17020-17024, XP-002283177, (2002).

* cited by examiner

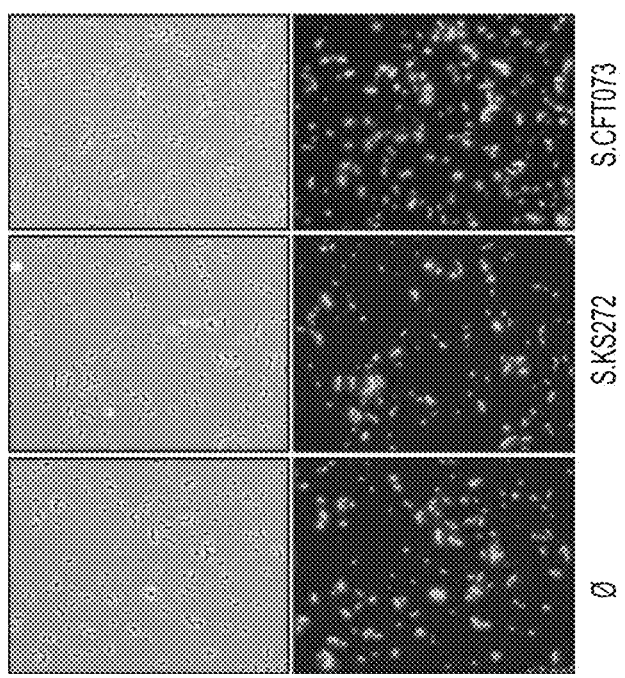
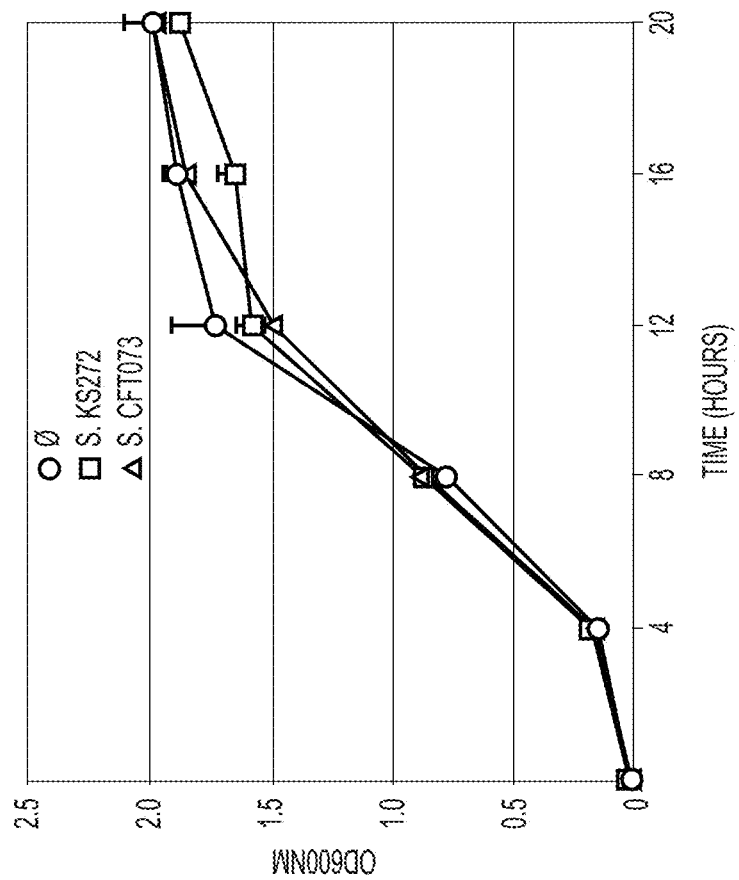
FIG. 1E
FIG. 1D

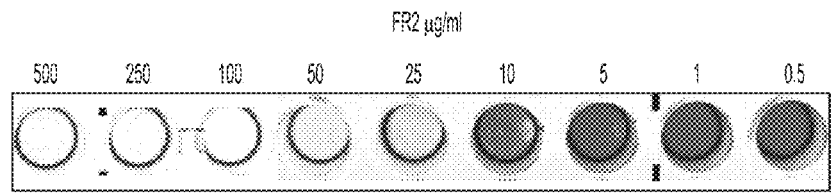
FIG. 10
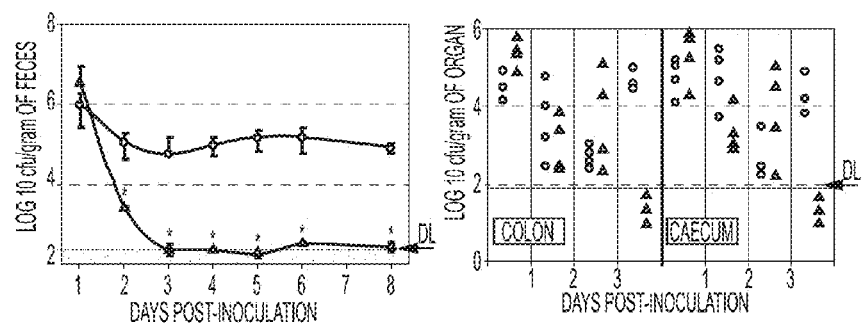
FIG. 11A          FIG. 11B
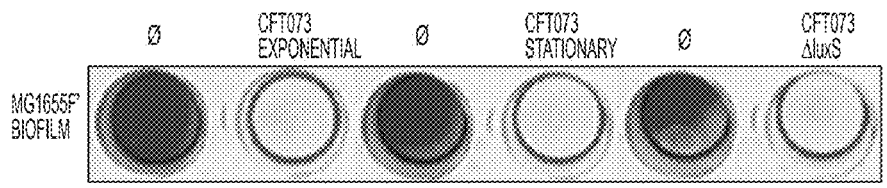
FIG. 12

USE OF BACTERIAL POLYSACCHARIDES FOR BIOFILM INHIBITION

FIELD OF THE INVENTION

The present invention pertains to the field of biofilm prevention. More particularly, the invention provides novel components which can prevent and/or inhibit bacterial biofilm formation on various surfaces.

BACKGROUND OF THE INVENTION

A biofilm is an accumulation of microorganisms embedded in a polysaccharide matrix and adherent to a biological or a non-biotic surface. Diverse microorganisms (bacteria, fungi, and/or protozoa, with associated bacteriophages and other viruses) can be found in these biofilms. Biofilms are ubiquitous in nature and are commonly found in a wide range of environments, including domestic and industrial water systems. Biofilms are also etiologic agents for a number of disease states in mammals.

Examples include infections of the oral soft tissues, teeth, middle ear, gastrointestinal tract, urogenital tract, airway/lung tissue, peritoneal membrane and eye. Biofilms also develop on medical indwelling devices, such as dental implants, urinary tract prostheses, peritoneal dialysis catheters, indwelling catheters for hemodialysis and for chronic administration of chemotherapeutic agents (Hickman catheters), cardiac implants such as pacemakers, prosthetic heart valves, ventricular assist devices (VAD), synthetic vascular grafts and stents, prostheses, internal fixation devices, percutaneous sutures, and tracheal and ventilator tubing.

Biofilm development in industrial devices such as water systems or agri-food plants also raises safety problems.

Planktonic bacteria (i.e., single-celled bacteria suspended in liquid media) are usually used as models for research and antibiotics design. However, bacteria in biofilms are far more resistant to antibiotics than their planktonic counterparts, and less accessible to the immune system. Moreover, conjugation occurs at a greater rate between cells in biofilms than between planktonic cells. This increased opportunity for gene transfer among bacteria is important, since bacteria resistant to antimicrobials or chemical biocides can transfer the genes for resistance to neighboring susceptible bacteria. Gene transfer can also convert a previous avirulent commensal organism into a highly virulent pathogen.

Biofilm formation is not limited to the attachment of bacteria to a surface. Indeed, when growing in depth, biofilm bacteria interact more between each other than with the actual physical substratum on which the biofilm initially developed. In a biofilm, bacteria can communicate through chemical signalling mechanisms, so that the community undergoes phenotypic changes when a minimum density (the quorum) is reached in the biofilm. This phenomenon, called "quorum sensing", can be responsible for the expression of virulence factors.

Besides E. coli biofilm-related polysaccharides such as colanic acid polymer, cellulose and (1-6) β-N-acetyl-glucosamine, E. coli isolates also produce two serotype-specific surface polysaccharides: the lipopolysaccharide (LPS) O antigen and capsular polysaccharide K antigen. These two classes of surface exposed polysaccharidic polymers have been shown to play indirect roles in biofilms by shielding of bacterial surface adhesin (Schembri et al., 2004).

The strategies described to date for preventing and/or disrupting biofilms are mainly based on quorum sensing inhibitors (Schachter, 2003).

SUMMARY OF THE INVENTION

The present invention provides a novel strategy for inhibiting biofilm formation, since the inventors have demonstrated, using in vitro mixed-species bacterial biofilm, that some bacteria release in the culture supernatant a soluble group II capsular polysaccharide that prevents biofilm formation by a wide range of Gram-negative and Gram-positive bacteria. As described in the experimental part below, these capsule components induce physico-chemical alterations of surface, leading to a reduction of cell-surface and cell-cell contacts that limits both initial adhesion and bacterial biofilm development.

A first object of the present invention is hence the use of a soluble group II-like capsular polysaccharide from a bacterial strain, for the preparation of a composition which prevents or inhibits adhesion of micro-organisms and/or biofilm development, in particular bacterial adhesion and/or bacterial biofilm development. In what follows, the term "polysaccharide", although used in the singular, can designate a mixture of different polysaccharides. The capsular polysaccharides produced by the bacteria are indeed of various sizes. In fact, E. coli capsules, which constitute the outermost protective layer of the cell surface, are classified into four groups based on genetic and biosynthetic criteria. Group II capsule is one of the 4 capsular types described in E. coli, and is constituted of high molecular weight and charged polysaccharidic polymers produced by most uropathogenic Escherichia coli (UPEC) and other extra-intestinal E. coli. Group II capsule displays a conserved modular genetic organization characterized by 3 functional regions. Region 1 (kpsFEDCUS) and region 3 (kpsMT) are conserved in all group II capsulated bacteria and encode proteins required for ABC-dependent export. Region 2 encodes a diversity of polysaccharidic structural components such as K1, K2 (CFT073), K5 and K96 capsular serotypes (Whitfield, 2006; Whitfield and Roberts, 1999). Group II-like capsules have also been described in Hemophilus influenzae and in Neisseria meningitides(Roberts, 1996).

In a preferred embodiment of the invention, a soluble group II-like capsular polysaccharide is obtained in the supernatant of a culture of bacteria selected amongst Escherichia coli, Hemophilus influenzae and Neisseria meningitidis. However, in the present text, the phrase "group II-like capsular polysaccharides" can designate capsular polysaccharides which are produced by other bacteria, provided they retain the anti-biofilm properties observed for the capsular polysaccharides produced by the above-mentioned strains. For example, capsular polysaccharides produced by the strain 47 of the ECOR collection (Ochman and Selander, 1984) are herein considered as a "group II-like capsular polysaccharide", although this strain apparently produces a hybrid group II/group III capsule.

The present invention can be performed with polysaccharides having different purification levels. For example, the crude supernatant of a bacterial culture (separated from the bacteria by filter-sterilizing or centrifugation) can be used according to the invention as a composition comprising soluble group II-like capsular polysaccharides. However, in order to increase the anti-biofilm activity of the composition, as well as its safety, the soluble group II-like capsular polysaccharide can be obtained as a purified fraction. Three levels of purification are described in the experimental part below, as non-limitative examples. Alternatively, a composition according to the invention can be obtained directly from the bacterial culture, for example after lysis of the bacteria.

Another object of the present invention is a composition for inhibiting bacterial adhesion and/or bacterial biofilm development, which comprises a soluble group II-like capsular polysaccharide from a bacterial strain. Such a composition can comprise polysaccharides having different purification levels. In a preferred embodiment, such a composition comprises a purified fraction of the supernatant of a culture of bacteria selected amongst *E. coli, H. influenzae* and *N. meningitidis*, comprising soluble group II-like capsular polysaccharides.

The present invention also relates to a process for purifying an anti-biofilm group II-like capsular polysaccharide from a bacterial strain, comprising the following steps:

(i) separating the supernatant of a culture of a bacterial strain expressing a group II-like capsule from the bacterial cells, (ii) precipitating the polysaccharides present in the obtained supernatant, and (iii) optionally, resuspending the precipitate.

The above process is preferably performed with a bacterial strain selected amongst *E. coli, H. influenzae* and *N. meningitidis*, more preferably with an uropathogenic *E. coli*.

In this process, step (i) can be carried out by centrifuging and/or filter-sterilizing the bacterial culture, in order to eliminate the bacterial cells. For example, in industrial processes, tangential filtration can be performed without any preliminary centrifugation. Tangential filtration can be performed continuously.

The skilled artisan can use any precipitation process known in the art to perform the second step of the above-described process. For example, the precipitation in step (ii) can be performed with three volumes of ethanol for one volume of supernatant.

In an advantageous variant of the process according to the invention, the precipitate obtained in step (ii) is first resuspended in water, dialyzed against deionised water, and then lyophilized before step (iii).

The resuspension in step (iii) can be done in water or in any buffer suitable for the intended use. An example of buffer which can be used is TrisHCl 20 mM, pH 7.5, with 25% propanol-1.

At the end of step (iii), the anti-biofilm polysaccharides are obtained as a semi-purified product, which can be used as such according to the invention, especially in applications which do not need medical-grade products.

In order to further purify the polysaccharides, the purification process can comprise an additional step (iv) of purification by chromatography, especially ion exchange chromatography, for example using a DEAE-Sepharose column. In this embodiment of the invention, an optional centrifugation step can be performed between step (iii) and step (iv), to discard the insoluble fraction.

The skilled artisan can choose any appropriate buffer for performing step (iv). An example of buffer which can be used is TrisHCl 20 mM, pH 7.5, with 25% propanol-1. According to an advantageous embodiment of the process, the precipitate is resuspended in TrisHCl 20 mM, pH 7.5, with 25% propanol-1 in step (iii), and the column used in step (iv) is equilibrated with the same buffer.

When performing a step of purification by ion-exchange chromatography, the group II-like capsular polysaccharides can be eluted using a salt gradient, for example a NaCl gradient. In an efficient embodiment of the process, described in the experimental part, the group II-like capsular polysaccharides are eluted with 300 mM NaCl in TrisHCl 20 mM, pH 7.5, 25% propanol-1.

Of course, the soluble group II-like capsular polysaccharides obtained through a process as above-described can be used, according to the invention, for the preparation of a composition which prevents or inhibits bacterial adhesion and/or bacterial biofilm development. An anti-biofilm composition comprising such purified polysaccharides is also part of the present invention.

In a particular embodiment, the composition of the present invention is formulated for preventive or therapeutic administration to a subject in need thereof. Non-limitative examples of compositions according to this aspect of the invention are oral solutions, solutions for infusion into the ear, collyrium, toothpaste or therapeutic dentifrice, etc. These compositions can be used, for example, to prevent the (re)-colonization of the gut, the lung, the ear, the sinus or any other organ or cavity, by pathogenic bacteria.

In another embodiment, the composition according to the invention is a liquid or a paste, for example a paint, which can be applied on any kind surfaces in order to prevent biofilm formation on these surfaces.

Another aspect of the present invention is an anti-biofilm coating, comprising a group II-like capsular polysaccharide from a bacterial strain. In such a coating, the group II-like capsular polysaccharide can have different purification levels, as described above. In a preferred embodiment of the coating according to the invention, the group II-like capsular polysaccharide is from a bacterial strain selected amongst *Escherichia coli, Hemophilus influenzae* and *Neisseria meningitidis*. This coating can be obtained, for example, by application of a composition as above-described. It can also be in the form of sheets which can be applied on any kind of device on which biofilm formation must be avoided.

Accordingly, a medical or industrial device, which is at least partly coated with an anti-biofilm coating comprising a group II-like capsular polysaccharide from a bacterial strain, is also part of the present invention. Such an object can be obtained, for example, by dipping part of the device or the whole device, into a liquid composition as described above. The skilled artisan can choose the incubation duration, depending on the material, the concentration of the composition in group II-like capsular polysaccharide, the intended use, and the like. Typically, said incubation can last from 10 seconds to 30 minutes. Short incubations (to 5 minutes) are usually sufficient. If necessary, the coated device can then be sterilized by a variety of treatments, without damaging the coating. For example, it can be intensively washed and/or autoclaved. Any kind of device made of glass, pyrex, PVC, polycarbonate, polypropylene and the like, can advantageously be coated according to this aspect of the invention.

Non-limitative medical devices which can advantageously be coated according to this aspect of the invention are scalpels, burs and other non-disposable surgery and/or dentistry tools, and indwelling devices, such as dental implants, urinary tract prostheses, peritoneal dialysis catheters, indwelling catheters for hemodialysis and for chronic administration of chemotherapeutic agents (Hickman catheters), cardiac implants such as pacemakers, prosthetic heart valves, ventricular assist devices (VAD), synthetic vascular grafts and stents, prostheses, internal fixation devices, percutaneous sutures, and tracheal and ventilator tubing.

Non-limitative examples of industrial devices which can advantageously be coated according to this aspect of the invention are plumbing materials, such as pipes, tubes, valves and the like, air-cooled towers, warm water systems, coolant circuits of nuclear power plant, especially secondary and tertiary circuits, agri-food materials, such as silos, fermenters, colanders, etc., furniture elements such as lab tables, counter tops and the like, especially for clean rooms, etc.

BRIEF DESCRIPTION OF THE DRAWINGS

The invention is further illustrated by the following figures and examples.

Figure Legends

FIGS. 1A to 1F: Biofilm inhibitory effect of CFT073. A, Biofilm formation of MG1655 F' in microfermentors inoculated with 1 or 10 $OD_{600\ nm}$ equivalent of KS272 (grey) or CFT073 (black) cells. MG1655F' biofilm alone (θ, white). Results are average of 6 replicates+/−.s.d. P<0.001 compared with MG1655F' biofilm. B, Microtiter plate MG1655F' biofilm alone (θ), or in the presence of KS272 or CFT073 supernatant, (S.KS272 and S.CFT073, respectively). C, MG1655F' biofilm in microfermentors perfused with medium without supernatant (θ) or with S.KS272 or S.CFT073. D, Growth curves of MG1655F' alone (θ) or with S.KS272 or S.CFT073. E, MG1655F' cell viability alone (θ) or with S.KS272 or S.CFT073 visualized with BacLight staining. F, Qualitative analysis of the biofilm formation in microtiter plate by different bacteria in the presence of CFT073 supernatant (S. CFT).

FIG. 10: Anti-biofilm activity of the FR2 fraction. CFT073 supernatant purified fraction (FR2) was added to the MG1655F' culture in concentrations ranging from 0.5 to 500 μg/ml. Biofilm formation of MG1655F' was visualized after 24 h. Concentration of 50-100 μg/ml inhibited MG1655 F' biofilm.

FIGS. 11A to 11B: Intestinal colonization by CFT073 and CFT073ΔR1. a, Bars represent the standard error of the log 10 mean number of CFU per gram of feces; a Mann-Whitney test was used for statistical analysis, the level of statistical significance (*) was set at P values of <0.016. b, Colon and caecium colonization by CFT073 (circles) and CFT073ΔR1 (triangles). DL: Detection limit.

FIG. 12: Effect of growth phase and quorum-sensing in the anti-biofilm properties of CFT073 supernatant. Biofilm formation of MG1655F' in microtiter plate in presence of supernatants purified from cells in exponential phase, stationary phase and AluxS mutant. 10.sup.10 cells in exponential phase ($OD_{600}$ nm=0.4) and in stationary phase ($OD_{600}$ nm=2) were centrifuged and supernatants were precipitated with 3 volumes of ethanol. The supernatant of AluxS mutant was purified from an overnight culture.

EXAMPLES

Example 1

Methods

Figure 1B:
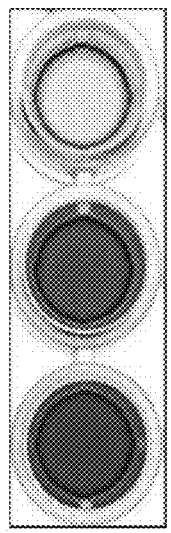
Figure 1C:
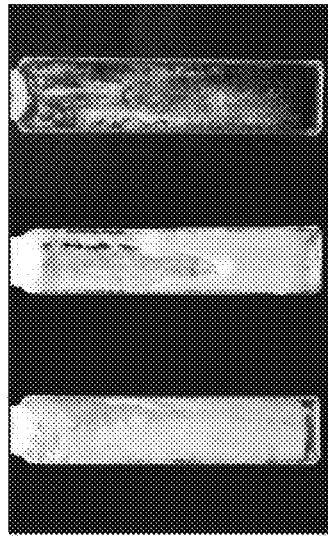

Bacterial Strains, Growth Conditions and Microscopy Analysis

Bacterial strains are listed in Table 1 below. Gram-negative bacteria were grown at 37° C. in M63B1 minimal medium with 0.4% glucose (M63B1 glu) or in LB rich medium. Gram-positive bacteria were grown in TSB with 0.25% glucose (TSBglu) at 37° C. The effect of CFT073 supernatant on bacterial growth and viability rate was evaluated using growth curve determination, colony forming unit count on LB plate and BacLight Live/Dead viability stain (Molecular Probes). Ferritin-staining and Scanning Electronic Microscopy was performed as described in (Bahrani-Mougeot et al., 2002). Epifluorescence and transmitted light microscopy were acquired using a Nikon E400 microscope. Autoaggregation assays were performed as described in (Beloin et al., 2006).

TABLE 1

Strains Used in This Study

| Strains | Relevant characteristics | References |
|---|---|---|
| *E. coli* strains | | |
| CFT073 | UPEC group II capsule (K2) | (Mobley et al., 1990) |
| MG1655F' | MG1655 F'tet-ΔtraD plasmid | (Ghigo, 2001) |
| KS272 | Commensal *E. coli* K-12 | (Strauch and Beckwith, 1988) |
| 1091 | Commensal *E. coli* | C. Le Bouguenec |
| 1092 | Commensal *E. coli* | C. Le Bouguenec |
| 1094 | Commensal *E. coli* | (Da Re and Ghigo, 2006) |
| 1096 | Commensal *E. coli* | C. Le Bouguenec |
| 1097 | Commensal *E. coli* | C. Le Bouguenec |
| 1102 | Commensal *E. coli* | C. Le Bouguenec |
| 1103 | Commensal *E. coli* | C. Le Bouguenec |
| 1110 | Commensal *E. coli* | C. Le Bouguenec |
| 1125 | Commensal *E. coli* | C. Le Bouguenec |
| 1127 | Commensal *E. coli* | C. Le Bouguenec |
| U-1 | UPEC group II capsule | C. Forestier |
| U-2 | UPEC group II capsule (K2) | C. Forestier |
| U-3 | UPEC non-group II capsule | C. Forestier |
| U-4 | UPEC group II capsule | C. Forestier |
| U-5 | UPEC group II capsule | C. Forestier |
| U-6 | UPEC group II capsule (K2) | C. Forestier |
| U-7 | UPEC non-group II capsule | C. Forestier |
| U-8 | UPEC group II capsule | C. Forestier |
| U-9 | UPEC group II capsule | C. Forestier |
| U-10 | UPEC group II capsule | C. Forestier |
| U-11 | UPEC non-group II capsule | C. Forestier |
| U-12 | UPEC group II capsule | C. Forestier |
| U-13 | UPEC group II capsule | C. Forestier |
| U-14 | UPEC non-group II capsule | C. Forestier |
| U-15 | UPEC group II capsule | C. Forestier |
| U-16 | UPEC group II capsule | C. Forestier |
| U-17 | UPEC non-group II capsule | C. Forestser |
| U-18 | UPEC non-group II capsule | C. Forestier |
| U-19 | UPEC group II capsule | C. Forestier |
| U-20 | UPEC group II capsule | C. Forestier |
| U-21 | UPEC group II capsule (K2) | C. Forestier |
| 984 | Commensal *E. coli* group II capsule (K1) | M. C. Ploy |
| 988 | Commensal *E. coli* group II capsule (K1) | M. C. Ploy |
| 999 | Commensal *E. coli* group II capsule (K1) | M. C. Ploy |
| 1007 | Commensal *E. coli* group II capsule (K1) | M. C. Ploy |
| 1014 | Commensal *E. coli* group II capsule (K1) | M. C. Ploy |
| IHE3034 | *E. coli* causing meningitis group II capsule (K1) | (Meier et al., 1996) |
| EcoR strains | *E. coli* Reference Collection (72 strains) | (Ochman and Selander, 1984) |
| Other bacteria | | |
| 15981 | *S. aureus* clinical strain | (Valle et al., 2003) |
| V329 | *S. aureus* bovine mastitis subclinical isolate | (Cucarella et al., 2001) |
| O-47 | *S. epidermidis* clinical strain | (Heilmann et al., 1996) |
| CH845 | *S. epidermidis* clinical strain BM94314 | (Galdbart et al., 2000) |
| 54 | *E. faecalis* clinical strain | (Toledo-Arana et al., 2001) |
| 11279 | *E. faecalis* clinical strain | (Toledo-Arana et al., 2001) |
| KP21 | *Klebsiella pneumoniae* strain | C. Forestier |
| PAK | *Pseudomonas aeruginosa* | (Vasseur et al., 2005) |
| 8013 | *Neisseria meningitidis* strain, serogroup C, class 1 | (Deghmane et al., 2002) |

TABLE 1-continued

Strains Used in This Study

| Strains | Relevant characteristics | References |
|---|---|---|
| Mutants | | |
| 44H3 | CFT073 kpsD::TnSC189 | This study |
| 25F11 | CFT073 kpsD::TnSC189 | This study |
| 23D5 | CFT073 kpsU::TnSC189 | This study |
| 16B9 | CFT073 kpsU::TnSC189 | This study |
| 14E12 | CFT073 kpsC::TnSC189 | This study |
| 76H11 | CFT073 kpsS::TnSC189 | This study |
| 30H8 | CFT073 kpsM::TnSC189 | This study |
| ΔkpsD | CFT073 kpsD::km | This study |
| ΔkpsC | CFT073 kpsC::km | This study |
| ΔkpsU | CFT073 kpsU::km | This study |
| ΔkpsS | CFT073 kpsD::km | This study |
| ΔkpsM | CFT073 kpsM::km | This study |
| Δ3692 | CFT073 Δ3692::km | This study |
| Δ3693 | CFT073 Δ3693::km | This study |
| Δ3694 | CFT073 Δ3694::km | This study |
| Δ3695-96 | CFT073 Δ3695Δ3696::km | This study |
| ΔR1 | CFT073 with a deletion from kpsD to kpsS | This study |
| ΔR2 | CFT073 with a deletion from c3692 to c3696 | This study |
| ΔR3 | CFT073 with a deletion from kpsT to kpsM | This study |
| U-9 ΔkpsD | U-9 kpsD::km | This study |
| U-15 ΔkpsD | U-15 kpsD::km | This study |
| IHE3034 ΔkpsD | IHE3034 kpsD::km | This study |
| ΔluxS | CFT073 ΔluxS | This study |
| CFT073gfp | CFT073λATTgfp | This study |
| ΔR1gfp | ΔR1λATTgfp | This study |
| ΔoxyR | MG1655 oxyR::km | (Beloin et al., 2006) |
| ompR234 | MG1655 ompR234 malA::km | (Vidal et al., 1998) |

Biofilm Formation Procedures

Microfermentors experiments: Biofilm was performed as described previously (Ghigo, 2001). Mixed biofilm cultures: an 8 hours MG1655F' biofilm formed in the internal microfermentors glass slide was infected with 1 $OD_{600\ nm}$ equivalent of CFT073-gfp overnight culture. After 24 hours of continuous culture in M63B1 glu, pictures of the glass slides were taken. Biofilm biomass was estimated by determining the $OD_{600\ nm}$ of the resuspension of the biofilm formed on the internal glass slide (Ghigo, 2001). Biofilm inhibition assays: the incoming medium was mixed in a 1:1 ratio with filtered supernatants and brought into the microfermentors at different time after bacteria inoculation (0, 1, 6 or 24 hours). The biofilm was further cultivated for an additional 24 hours before biomass determination. Analysis of bacterial interaction with treated surfaces: the glass slides were incubated 1 min with filtered CFT073 supernatant and rinsed once in deionised water prior to inoculation in microfermentors. Biofilm formation on the slide was determined after 24 hours.

Microtiter plate experiments. Static biofilm formation assay were performed in 96-well PVC microtiter plates (Falcon) as described in (O'Toole and Kolter, 1998).

Biofilm inhibition assays: overnight cultures were adjusted to $OD_{600}$=0.04 before inoculating 100 µl in 96-well plates in the presence or absence of 50 µl of supernatant.

Flow-chamber experiments. Biofilms were performed in M63B1 glu at 37° C. in 3× channels flow-cells (1×4×40 mm). The flow system was assembled and prepared as described in (Christensen et al., 1999). Inocula were prepared as follows: 16-20 hours old overnight cultures in M63B1 glu were harvested and resuspended as normalized dilutions ($OD_{600}$=0.005). 300 µl were injected into each flow channel. Input medium was mixed in a 1:1 ratio with filtered supernatant. Flow was started 1 h after inoculation at a constant rate of 3 ml $h^{-1}$ using a Watson Marlow 205 S peristaltic pump. All Assays were at least performed in triplicate.

Purification of CFT073 or Other Group II Capsulated Strain Supernatants Displaying Anti-Biofilm Activity Three levels of purification have been tested:

(i) Filtration (sterilization) of the active supernatants (S.CFT, used in all the experiments on microtiter plates or in microfermentors)

Overnight cultures in M63B1 glucose 0.4% were centrifuged for 30 min at 5000 rpm at 4° C. and filtered through 0.25 µm filter to eliminate bacteria.

(ii) Precipitation of polysaccharides contained in active supernatants

The polysaccharides contained in the filtered supernatant were precipitated with 3 volumes of ethanol, resuspended in deionized water and dialyzed against deionized water in 10 kDa cut-off dialysis cassettes (Pierce biochemical).

(iii) purification of the capsular polysaccharides active fraction (capsular active fraction FR2)

the partially purified supernatant active fraction obtained in step (ii) was lyophilized and resuspended in 80 ml of buffer Tris HCl 20 mM pH 7.5 containing 25% de propanol-1.

This resuspension was centrifuged for 10 minutes at 3000 rpm to eliminate the insoluble particles.

the soluble supernatant was loaded on a DEAE-Sepharose column (30 ml, 2.6×6 cm, Amersham) and equilibrated with Tris HCl 20 mM pH 7.5, 25% de propanol-1 buffer.

the column was washed with Tris HCl 20 mM pH 7.5, 25% propanol-1 buffer at the rate of 20 ml/h.

After the wash, the column was eluted with a NaCl gradient (0 to 1 M in 400 ml) and the polysaccharide concentration of each eluted fractions (4.5 ml) was tested by the Dubois method (Dubois et al., 1956): 100 µl of phenol at 5% and 500 µl of concentrated sulfuric acid followed by vortex agitation and read at 492 nm)

The positive fractions (about 10 fractions of 4.5 ml) were pooled together and dialyzed against deionized water and lyophilized 1 mg of the lyophilysate was resuspended in 1 ml of deionized water.

Handling of Culture Supernatants and Polysaccharide Analysis.

Overnight cultures in M63B1 glu at 37° C. were centrifuged 30 minutes at 5000 rpm at 4° C. After filtration of the supernatant with a 0.2 µm filter, macromolecules were precipitated with 3 volumes of ethanol and dialysed against deionised water using 10 kDa cassettes (Pierce). Total amounts of phosphate and neutral sugars were determined by ammonium molybdate/ascorbic acid and phenol/sulfuric acid methods, respectively. Polysaccharide composition was determined by HPLC (ion-exclusion column) and by gas liquid chromatography as in (d'Enfert and Fontaine, 1997; Fontaine et al., 2000). CFT073 supernatant active fraction, FR2, was purified using a DEAE-Sepharose column (Amersham) and eluted with 300 mM NaCl in 25% propanol-1.20 mM TrisHCl pH7.5. Molecular weight of the polymer was estimated by gel filtration chromatography on Superdex-200 (Amersham) using dextran as standard. Polysaccharide degradations were done by total acid hydrolysis (trifluoroacetic acid, 4N, 4H, 100° C.) or by aqueous hydrofluoric acid (48% aq. HF, 2 days on water-ice).

Mutagenesis and Molecular Techniques.

Mariner transposon mutagenesis of *E. coli* CFT073 was performed as described in (Da Re and Ghigo, 2006). The supernatants of 10,000 transposon mutants incubated 24 h, in LB at 37° C. in 96-well microtiter plates were extracted after centrifugation of the plates 15 min at 10000 rpm and their effect on MG1655F' biofilm formation was analysed. Transposon insertion sites were determined as described in (Da Re and Ghigo, 2006). Homology searches were performed using Blast 2.0. Deletion mutants were generated as detailed at http://www.pasteur.fr/recherche/unites/Ggb/3SP-CRprotocol.html, using primers presented in Table 2.

TABLE 2

Primers used in this study

| Target gene Primers used to generate deletion mutants | Primer name | Sequence | SEQ ID No. |
|---|---|---|---|
| kpsD | KpsD.500-5 | gaccagcttgcctttgcagaaacg | 1 |
|  | KpsD.500-3 | cttttcagcattacgcggatagg | 2 |
|  | KpsD.GB.L-5 | TGCTCGATGAGTTTTTCTAAGGAGTTGAAatgagcaa | 3 |
|  | KpsD.GB.L-3 | gattttgagacacaacgtggctttCATcacAAACTCATTCAGCGACA | 4 |
|  | KpsD.ext-5 | ttgcgcttaagtttaaccaaaccg | 5 |
|  | KpsD.ext-3 | gctctggcatggactccggtaact | 6 |
| kpsU | KpsU.500-5 | atgaacgcagttcagctttatcgcc | 7 |
|  | KpsU .500-3 | ccaaatttcggcttgaggatttc | 8 |
|  | KpsU.GB.L-5 | TGCTCGATGAGTTTTTCTAAcaggaactggctgaaaacgcatga | 9 |
|  | KpsU.GB.L-3 | gattttgagacacaacgtggctttCATTTCAACTCCttacaaagacaga | 10 |
|  | KpsU.ext-5 | tgcagaacggcgataccttaatcg | 11 |
|  | KpsU.ext-3 | ctcggcaatcaaacgtactcgttg | 12 |
| kpsC | KpsC.500-5 | gaggcagatatcaacattaacc | 13 |
|  | KpsC.500-3 | gttgaaggttttaagttctcaac | 14 |
|  | KpsC.GB.L-5 | TGCTCGATGAGTTTTTCTAAACAATTTCATAGTTGACTATTAC | 15 |
|  | KpsC.GB.L-3 | gattttgagacacaacgtggctttgagtaaatgccaatcatgcgttttc | 16 |
|  | KpsC.ext-5 | cgactcacattacgattatgcg | 17 |
|  | KpsC.ext-3 | gaaaatgatttgtggtggcggtagc | 18 |
| kpsS | KpsS.500-5 | agagcaaccttgagttattacg | 19 |
|  | KpsS.500-3 | aaagacaagggatagctttagg | 20 |
|  | KpsS.GB.L-5 | TGCTCGATGAGTTTTTCTAATTTATTCTAAATTATCAACG | 21 |
|  | KpsS.GB.L-3 | gattttgagacacaacgtggctttCATAAATAATCTGTGTAATAGTCAA | 22 |
|  | KpsS.ext-5 | agcgactggttgaaagcaaactg | 23 |
|  | KpsS.ext-3 | ttcgatgagtcaagactattgg | 24 |
| kpsM | KpsM.500-5 | TTACTACGCATAAAATTCATGG | 25 |
|  | KpsM.500-3 | aatgccatgcttaaaccaaagcc | 26 |
|  | KpsM.GB.L-5 | TGCTCGATGAGTTTTTCTAAcaatgctgacatcatgattaagattg | 27 |
|  | KpsM.GB.L-3 | gattttgagacacaacgtggctttcttgccatTTGGTGATGTGATCCT | 28 |
|  | KpsM.ext-5 | TCGCATGCGTTCTGGTTTGAG | 29 |
|  | KpsM.ext-3 | cacatcacaaaactctttcaatg | 30 |
| Kps | KpsD.500-5 | gaccagcttgccTtgcagaaacg | 31 |
|  | KpsS.500-3 | aaagacaagggatagctttagg | 32 |
|  | KpsD.GB.L-3 | gattttgagacacaacgtggctttCATcacAAACTCATTCAGCGACA | 33 |
|  | KpsS.GB.L-3 | gattttgagacacaacgtggcttCATAAATAATCTGTGTAATAGTCAA | 34 |
|  | KpsD.ext-5 | ttgcgcttaagtttaaccaaaccg | 35 |
|  | KpsS.ext-3 | ttcgatgagtcaagactattgg | 36 |

TABLE 2-continued

Primers used in this study

| Target gene Primers used to generate deletion mutants | Primer name | Sequence | SEQ ID No. |
|---|---|---|---|
| Kps | KpsR2.500-5 | atataggagtatggagcgaaac | 37 |
|  | KpsR2.500-3 | ttgagtaaggaatatggcttag | 38 |
|  | KpsR2.GB-L5 | TGCTCGATGAGTTTTTCTAAGAAATCAGACGAGTTTTC | 39 |
|  | KpsR2.GB-L3 | gattttgagacacaacgtggctttcataacatACTATGTCCCCATGATTATT | 40 |
|  | KpsR2.ext-5 | catgtactcattttcacgtaaag | 41 |
|  | KpsR2.ext-3 | tgctaaaattgcattattaggtc | 42 |
| Kps | KpsM.500-5 | TTACTACGCATAAAATTCATGG | 43 |
|  | KpsR3.500-3 | AATTAACCATATCTTTTGATTTGAG | 44 |
|  | KpsR3.GB-L5 | TGCTCGATGAGTTTTTCTAAatcagacttgtctttatcag | 45 |
|  | KpsM.GB.L-3 | gattttgagacacaacgtggctttcttgccatTTGGTGATGTGATCCT | 46 |
|  | KpsM.ext-5 | TCGCATGCGTTCTGGTTTGAG | 47 |
|  | KpsR3.ext-3 | cctagcaacaaaatatttagcgac | 48 |
| Kp95- | Kps95-96.500- | aaacaatatcatggccagtcgg | 49 |
|  | Kps95-96.500- | aataacgttcaggtattgaagg | 50 |
|  | Kps95-96.GB- | TGCTCGATGAGTTTTTCTAAccttgaGGTCTATATAACTGAA | 51 |
|  | Kps95-96.GB- | gattttgagacacaacgtggctttcatcaaatgtaccaaaggtgataac | 52 |
|  | Kps95-96.ext- | taaatcaacgttactgagaata | 53 |
|  | Kps95-96.ext- | gaatatccgagtgcataatacc | 54 |
|  | Kps95-96.500- | aaacaatatcatgaccaatcgg | 55 |
| C3694 | c3694.500-5 | aagcattagaattggaaccc | 56 |
|  | c3694.500-3 | cttttccatgtattcctctccaag | 57 |
|  | c3694.GB.L-5 | GATGAGTTTTTCTAAgtgcaagtatacttgtaaccc | 58 |
|  | c3694.GB.L-3 | GATTTTGAGACACAACGTGGCTTTCATatacgcatcaatagccttagccc | 59 |
|  | c3694.ext-5 | gcggagagctattttaaagcagg | 60 |
|  | c3694.ext-3 | cggaaaacgatatgacaatcctg | 61 |
| C3693 | c3693.500-5 | gtttattgttgcaggcatccaag | 62 |
|  | c3693.500-3 | atgccgttagatagttttattcc | 63 |
|  | c3693.GB.L-5 | TGCTCGATGAGTTTTTCTAAatggatgctcaaaaggaggtacg | 64 |
|  | c3693.GB.L-3 | GATTTTGAGACACAACGTGGCTTTCATcagcattggttggtaatgcatttg | 65 |
|  | c3693.ext-5 | acatattaacagtaatataacc | 66 |
|  | c3693.ext-3 | ctacaaatttggatactgcaaatc | 67 |
| C3692 | c3692.500-5 | ttatacttgcggtgatttgcag | 68 |
|  | c3692.500-3 | ATGACTCATAAAAATATATTCC | 69 |
|  | c3692.GB.L-5 | TGCTCGATGAGTTTTTCTAAtatttacagaataattactgg | 70 |
|  | c3692.GB.L-3 | GATTTGAGACACAACGTGGCTTTCAT taagccaatagtcttgactcatcg | 71 |
|  | c3692.ext-5 | aattcatatgattgtagcaatg | 72 |
|  | c3692.ext-3 | CAACGTAGAATAAAAGCATTACC | 73 |
| luxS | LuxS.500-5 | AAACTGCGCAGTTCCCGTTACC | 74 |
|  | LuxS.500-3 | CCTGATTTTGTTCCCTGGGAGG | 75 |
|  | LuxS.GB-L5 | TGCTCGATGAGTTTTTCTAATCAGTGGAACAAAAGAAG | 76 |
|  | LuxS.GB-L3 | gattttgagacacaacgtggctttcatTTAGCCACCTCCGGTAATTT | 77 |
|  | LuxS.ext-5 | CTGGAACCGGGTGATCCTCGAAG | 78 |
|  | LuxS.ext-3 | AGCAACAATGCTGGGGAAAAATGC | 79 |
| Primers used for |  |  |  |
|  | Kps95-F | aacgaaaattgcttgctctggc | 80 |
|  | Kps94-R | cggtgccaagtttgaaataacg | 81 |
|  | Kps94-F | gaaaatagtgtagacggtctcttc | 82 |
|  | Kps92-R | tttggatactgcaaatcaccgc | 83 |
|  | Kps11f | GCGCATTTGCTGATACTGTTG | 84 |
|  | KpsK2r | AGGTAGTTCAGACTCACACCT | 85 |

TABLE 2-continued

Primers used in this study

| Target gene Primers used to generate deletion mutants | Primer name | Sequence | SEQ ID No. |
|---|---|---|---|
| Primers used to check | | | |
| | KmGB.verif-5 | TGGCTCCCTCACTTTCTGGC | 86 |
| | KmGB.verif-3 | ATATGGCTCATAACACCCCTTG | 87 |
| Primers used for | | | |
| | ARB1 | ggCCACgCgTCgACTAgTACNNNNNNNNNNNgATAT | 88 |
| | ARB6 | ggCCACgCgICgACIAgTACNNNNNNNNNNACgCC | 89 |
| | ARB2 | ggCCACgCgTCgACTAgTAC | 90 |
| | 1R2 | CTgACCgCTTCCTCgTgCTTTACgg | 91 |
| | 1R2-60-5 | TTCTGAgcgggactctggggtacg | 92 |

Analysis of the Physico-Chemical Properties of the Active Fractions

Zeta potential was measured as in (Caruso et al., 1999) after 20 minutes of incubation of 10 μm in diameter cationic colloids latex particles with dialyzed precipitated supernatants (i.e., the level (ii) of purification indicated above). The latex particles bear permanent net positive charge due to their polyethylenimine (PEI) coating. The layer of PEI is a branched 6400 dalton molecular weight polymer bearing approximately 50% of methylated quaternary functions which confer a stable positive charge to the molecule. This polymer was deposited in aqueous phase on the initially carboxylated particles (Decher, 1997). Hydrophilic properties of the supernatants were investigated by determining the contact angle formed by a 2.5 μl ultrapure water droplet with a glass plane surface previously incubated in the supernatants for 20 minutes. Surface interactions were analyzed by monitoring the adsorption of propidium iodide on supernatant-treated cationic colloids. The affinity of the treated surfaces for the fluorescent probe was tested using flow cytometry (Leboeuf and Henry, 2006) and fluorescence microscopy. All incubations of particles with supernatant were performed at low particle/volume fraction (ca. 0.2%) likely leading to surface saturation by the active species.

In Vivo Mice Experiments

CFT073 and CFT073AR1 in vivo colonization were performed as described previously (Maroncle et al., 2006). Mice were intragastrically fed with 1010 CFU. Bacteria contained in fecal samples were numbered on agar plates. For examination of bacterial growth in the host, mice were sacrificed at various times after inoculation; colon and caecum were homogenized in physiological water, and plated to determine cfu per gram of tissue

Example 2

Anti-Biofilm Activity of CFT073 Supernatant

Figure 1A:
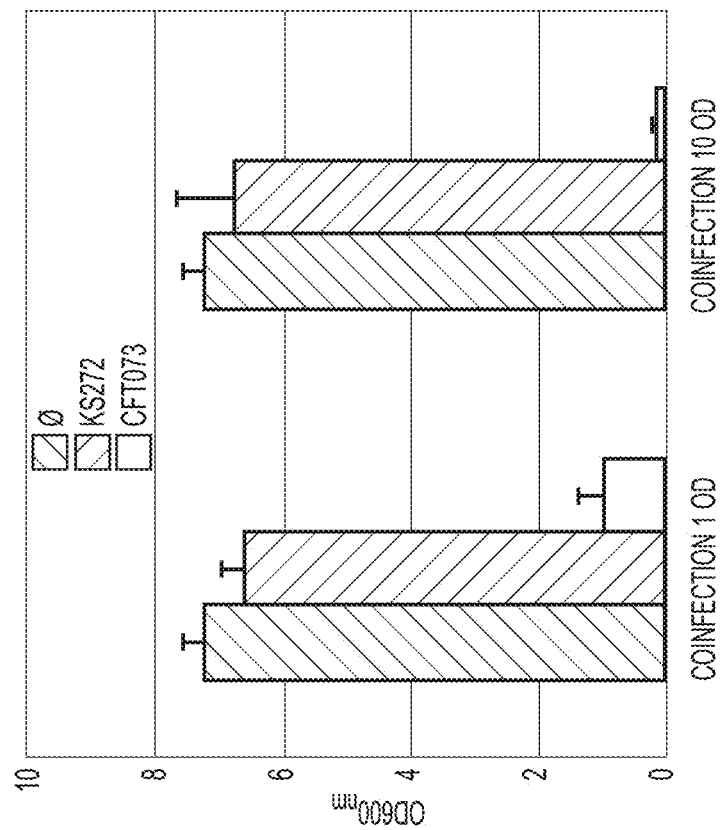

In order to study UPEC interactions within multicellular biofilm (Hall-Stoodley et al., 2004) bacterial communities, an in vitro mixed bacterial biofilm model in microfermentors was developed (Ghigo, 2001). Using this model, a 8 hours biofilm formed by the commensal strain of E. coli K12 MG1655 F' was inoculated with different titers of the UPEC strain CFT073, and further cultivated for 24 hours. Upon increasing titers of CFT073, a strong reduction of the E. coli K12 MG1655 F' biofilm development was observed, which was not observed when the commensal E. coli strain KS272 was used (FIG. 1A). This suggested that CFT073 could prevent MG1655 F' biofilm formation either by direct contact or by secretion of an inhibitory molecule. To distinguish between these two possibilities, the supernatant of CFT073 stationary phase culture was filter-sterilized and its effect on E. coli biofilm formation was tested. In the presence of CFT073 supernatant, MG1655 F' biofilm was severely affected (FIGS. 1B,C). This biofilm inhibition did not result from a growth defect due to a bactericidal or bacteriostatic activity, since MG1655 F' growth rate and cell viability were not affected by the CFT073 supernatant (FIGS. 1D,E).

Figure 1F:
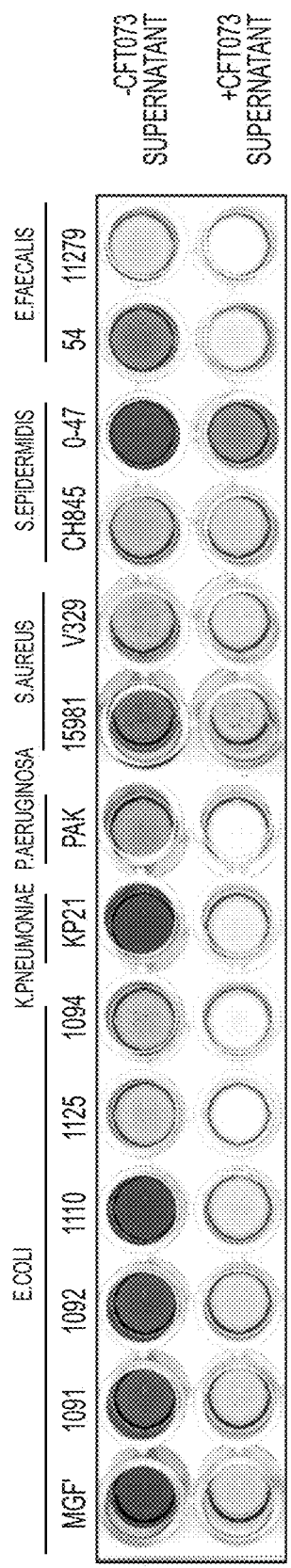

In order to determine the spectrum of the anti-biofilm activity of CFT073 supernatant, its effect was tested on several adherent bacteria (E. coli, Klebsiella pneumoniae, Pseudomonas aeruginosa, Staphylococcus aureus, S. epidermidis and Enterococcus faecalis). This analysis showed that CFT073 supernatant was active against a surprisingly wide range of bacteria, even in mixed cultures (FIG. 1F and FIG. 2).

Example 3

Correlation Between Anti-Biofilm Activity and Type-II Capsule

Figure 3A:
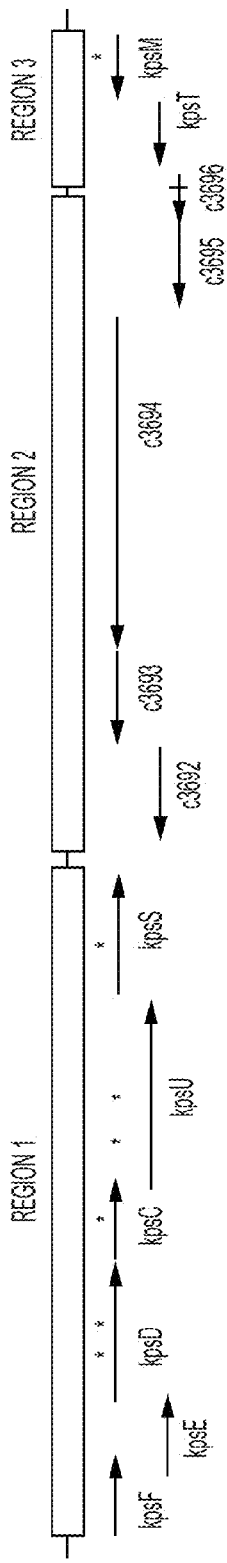
FIGS. 3A to 3D: Relationship between capsule production and anti-biofilm activity of the CFT073 supernatant. A, Genetic organization of the CFT073 capsule R1, R2 and R3 regions. Genes with transposon insertions are marked with an asterisk. B, Biofilm formation of MG1655F' cultivated in the presence of the capsule mutant supernatants. C, Hexose levels in the supernatants. kpsF, kpsU, c3692 and c3693 correspond to mutants that do not impair capsule production. D, Stationary phase CFT073 or CFT073Δ bacterial cell capsules stained with ferritin and examined by transmission electron microscopy (×100000; bar=0.2 μm) (left panel); 125 and 105 cells were observed respectively. Stained CFT073 capsule is indicated by an arrow. On the right panel: scanning electron micrographs of stationary-phase CFT073 or CFT073ΔkpsD (×50,000; bar=0.5 μm); 45 and 37 cells were observed respectively.
Figure 3B:
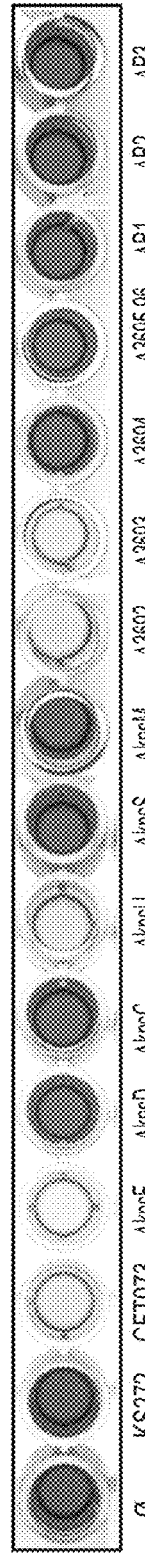
Figure 3C:
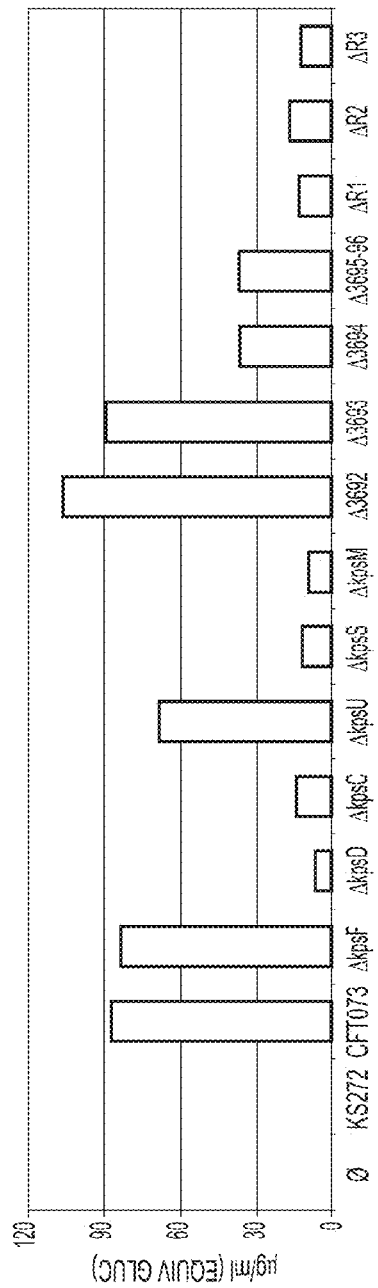
Figure 3D:
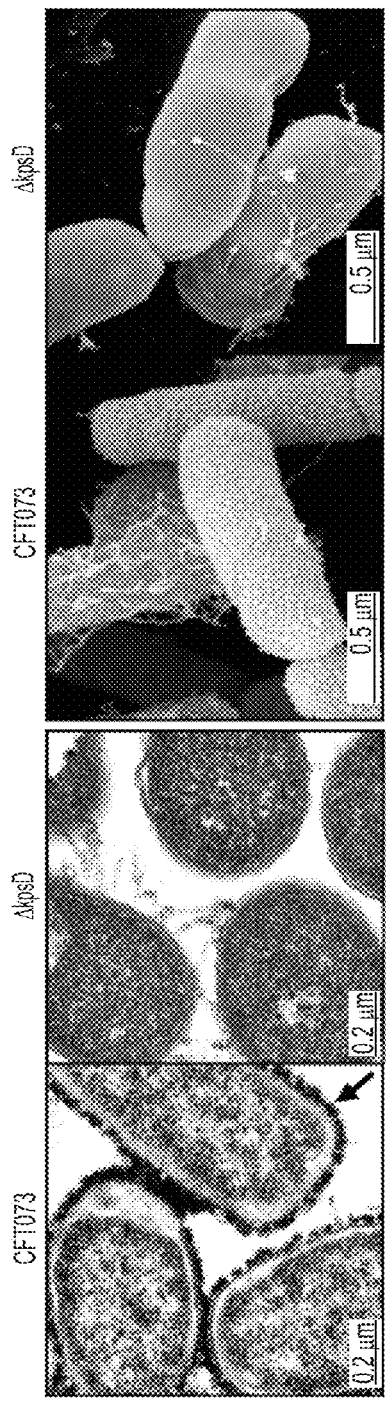

To elucidate the genetic basis of the anti-biofilm effect, the supernatant activity of ca. 10,000 CFT073 random mariner transposon insertion mutants was tested. The inventors identified seven candidates impaired in their ability to inhibit MG1655 F' biofilm formation. All these mutants mapped in genes involved in the expression of the group II capsular polysaccharide, the outermost bacterial cell surface structure (Whitfield and Roberts, 1999). Group II capsule displays a conserved modular genetic organization characterized by 3 functional regions (Roberts, 1996) (FIG. 3A). Region 1 (kpsFEDCUS) and region 3 (kpsMT) are conserved in all group II capsulated bacteria and encode proteins required for the ABC-dependent polysaccharide export. Region 2 is variable and encodes polysaccharide serotypes such as K1, K2 (CFT073), K5, K96 (Roberts, 1996). The R1, R2 or R3 region, or each individual kps gene was deleted and it was observed that, except for kpsU, c3692 and c3693, all the mutants lost the ability to inhibit *E. coli* biofilm formation, which correlated with a reduced amount of precipitated sugars in the supernatant (FIGS. 3B, 3C). While a ferritin-stained capsule could still be detected around CFT073 cells (FIG. 3D), these results indicated that the CFT073 capsule nevertheless undergoes a significant release into the medium supernatant that is responsible for the observed anti-biofilm effect.

Figure 4A:
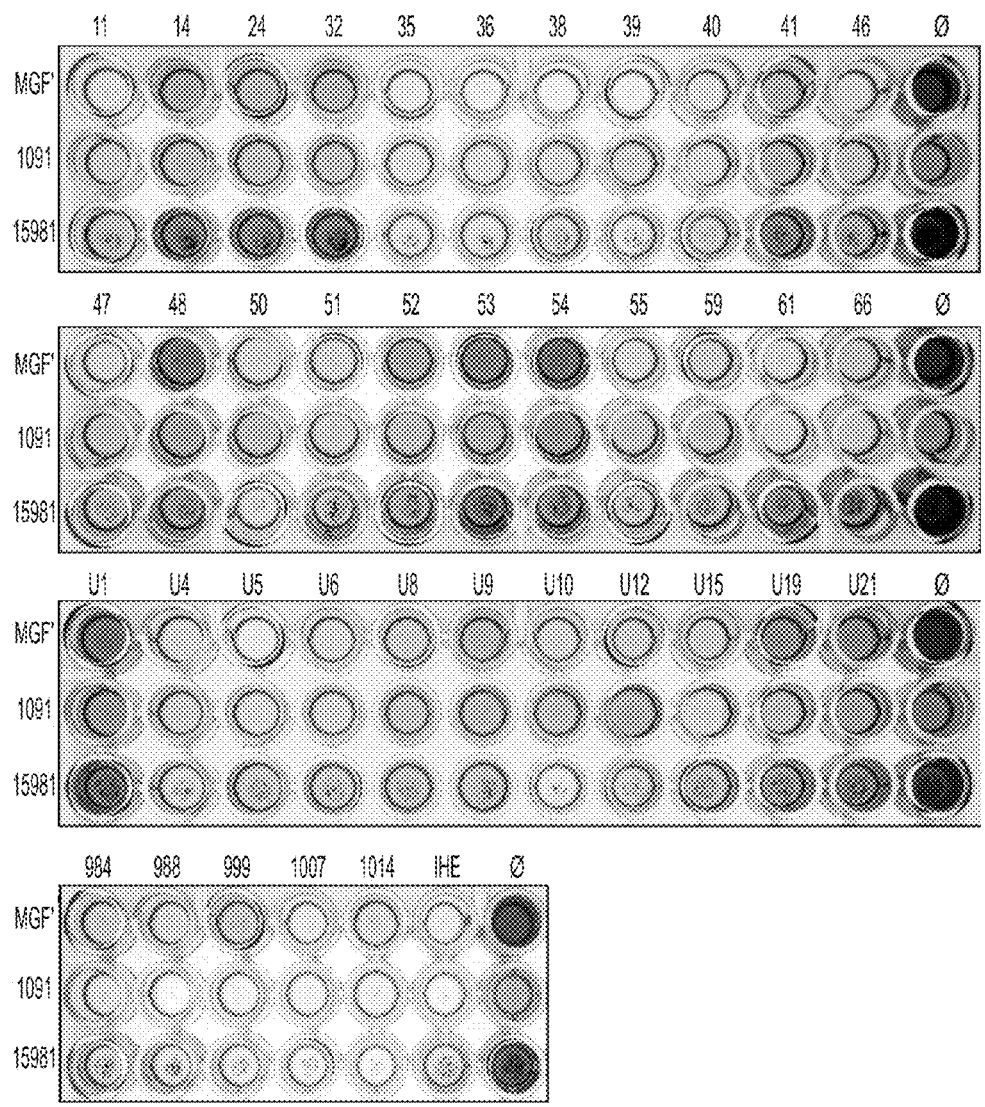
FIGS. 4A to 4C: Correlation between anti-biofilm activity and group II capsule. Biofilm formation of E. coli MG1655F' and 1091 strains, and of the S. aureus 15981 strain cultured with: (A) supernatants of E. coli exhibiting anti-biofilm activity (see Table 1) (beside strain 47, all the strains tested produce group II capsule) (B) supernatants of CFT073, U-9, U-15 strains and their respective kpsD mutants. (C) Biofilm formation in microfermentor of UPEC strains CFT073, U-9, U-15 (black) and their respective kpsD mutants (grey) grown in M63B1 glu, and kpsD mutants grown in media supplemented with their corresponding wild-type supernatant (white). Biofilms were grown for 36 h at 37° C. Error bars represent standard deviation of the mean. Strains identified by simple numbers correspond to those of the EcoR collection (Othman and Selander, 1984).
Figure 4C:
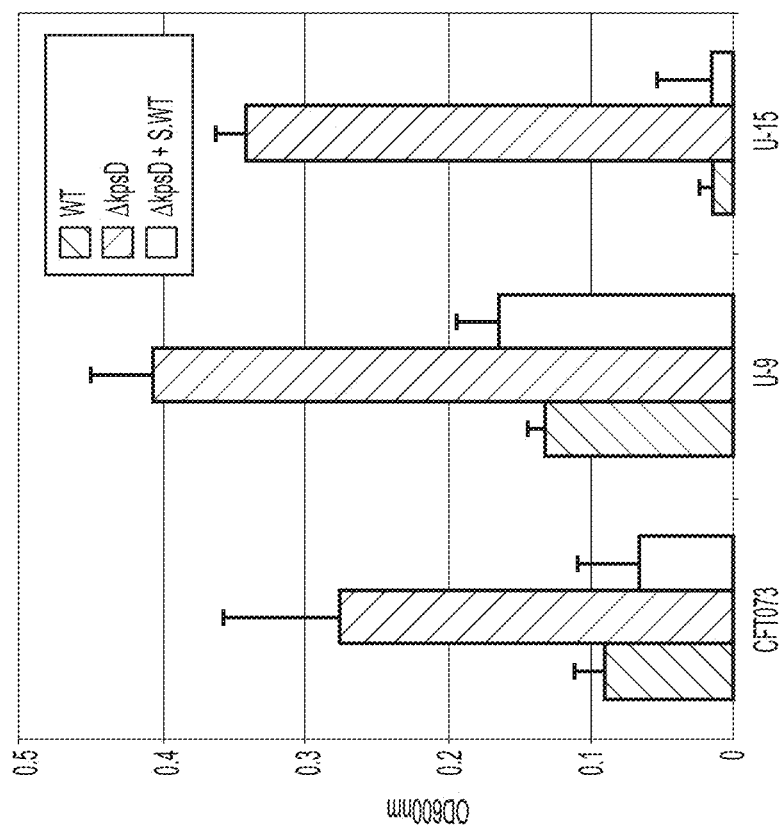
Figure 4B:
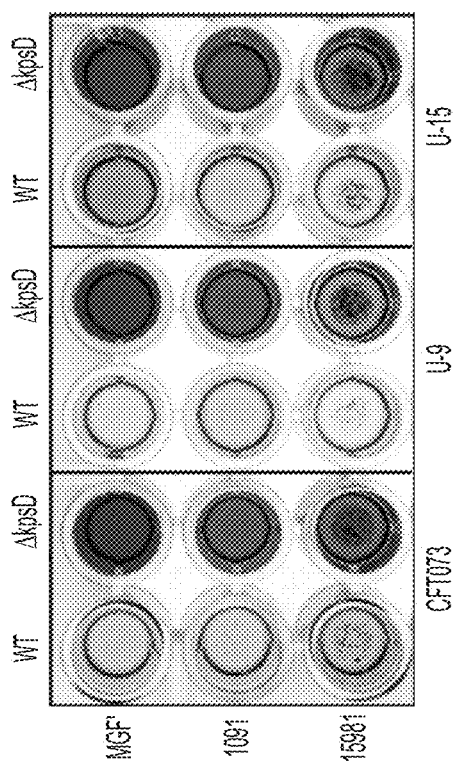

In order to determine whether biofilm inhibition was an exclusive property of *E. coli* CFT073 supernatant, the inventors screened several clinical uropathogenic bacterial isolates of *Klebsiella, Proteus, Enterobacter, Morganella, Citrobacter* and *Serratia*, as well as a collection of 110 *E. coli* strains of diverse origins. They found that only the filtered supernatant of 40 *E. coli*, including 17 UPEC, inhibited biofilm formation on a wide range of bacteria without affecting growth rate (FIG. 4A). Moreover, as CFT073 *E. coli* strain, all active strains are able to inhibit biofilm formation of adherent bacteria other than *E. coli* (in FIG. 4A see 15981 *S. aureus* biofilm data). Using specific PCR probes (Johnson and O'Bryan, 2004), they showed that 39 of the 40 active *E. coli* strains carried group II capsule genes. The 40$^{th}$ bacterium, EcoR47, seems in fact to produce a hybrid group II/group III capsule. This strain has been shown to carry group II KPS genes (Boyd and Hartl, 1998). Consistently, the introduction of a kpsD mutation into the clinical UPEC isolates U-9 and U-15 abolished the biofilm-inhibitory effect of their supernatants (FIG. 4B). Interestingly, although CFT073, U-9 and U-15 strains displayed a very limited ability to form biofilm in the microfermentor biofilm model, their respective kpsD mutants displayed an increased biofilm phenotype. This phenotype could be reverted upon the addition of CFT073 supernatant, suggesting that these strains could also self-inhibit their own adhesion (FIG. 4C).

Figure 5:
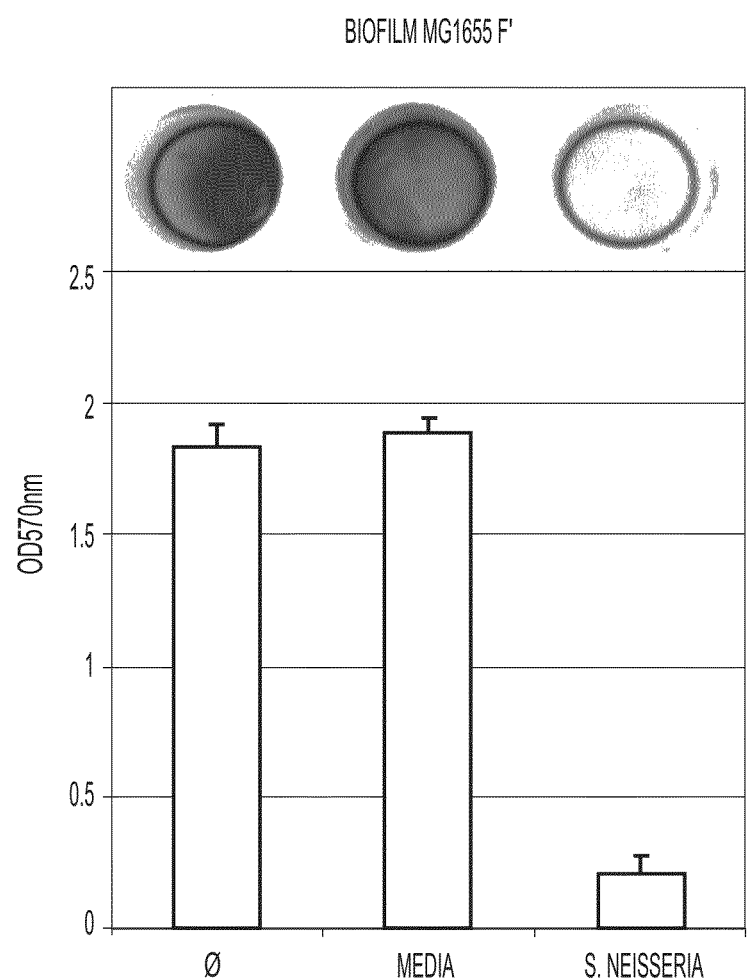
FIG. 5: Anti-biofilm effect of Neisseria meningitidis supernatant. Quantification of the microtiter plate biofilm formation of MG1655F' in the presence of S. Neisseria. $OD_{570\ nm}$ of the crystal violet dye was determined as described in (O'Toole and Kolter, 1998).

A biofilm formation inhibition test was also performed with a strain of *Neisseria meningitidis*, the capsule of which is biochemically very similar to the group II capsule of *E. coli*. Interestingly, the results show that the supernatant of *N. meningitidis* also inhibits the biofilm formation of *E. coli* MG1655F' (FIG. 5), demonstrating that anti-biofilm activity is a property not only of the group II capsule from *E. coli* but also of capsules known to be similar to the latter (i.e., group II-like capsules).

Example 4

Physico-Chemical Properties of the CFT073 Supernatant

Figure 6A:
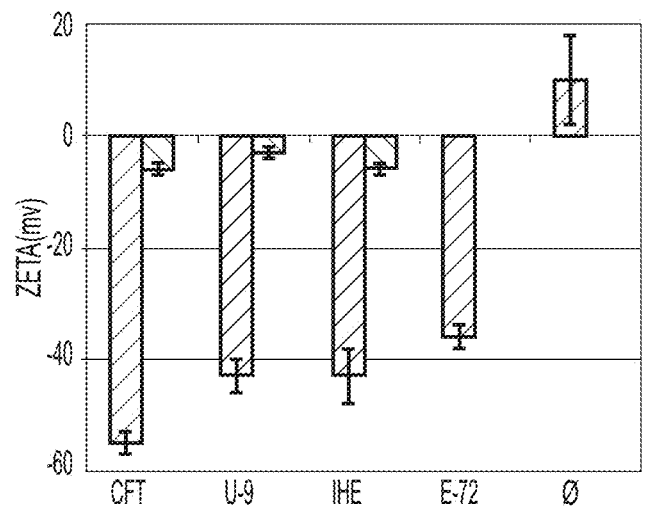
FIGS. 6A to 6D: Physico-chemical properties of the CFT073 supernatant. a, ξ potential of cationic colloids incubated with the dialyzed supernatants from: CFT073 (CFT), U-9, IHE3034 (IRE), EcoR72 (E-72) (dark grey) and their respective capsule mutants (light grey). (θ) correspond to M63B1 glu treatment. b, Water droplet contact angle on surface incubated with CFT, U-9, IHE, E-72 (dark grey) and the capsule mutants (light grey). c, Propidium iodide adsorption onto cationic particles incubated with CFT, U-9, IRE, E-72, FR2 (CFT073 supernatant purified fraction), (dark grey) and their respective capsule mutants (light grey). The extent of the adsorption is given by the fluorescent intensity (>670 nm). d, Fluorescence microscopy of cationic particles incubated with CFT, S.CFT073ΔR1 (ΔR1), FR2 and not incubated (θ). Error bars represent the standard deviation of the mean.
Figure 6B:
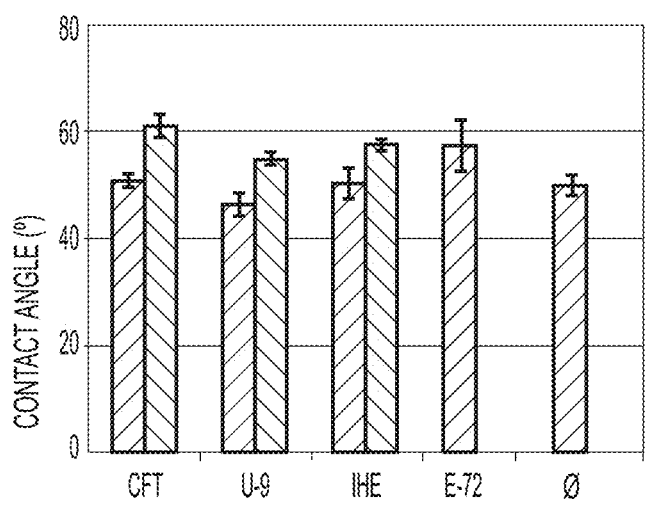

When the inventors analyzed the composition of the polysaccharidic fractions precipitated from the active supernatants of different group II capsule *E. coli* serotypes, including CFT073 (K2), U-9 (non-K2) and IHE3034 (K1), they observed, in agreement with previous studies (Jann et al., 1980; Silver and Vimr, 1984), that these fractions displayed significantly different compositions (data not shown). This suggested that, although biochemically distinct, group II capsules released by these strains could share a similar mode of action leading to biofilm inhibition. To further study the mechanisms by which group II capsule inhibit bacterial biofilm formation, these fractions were brought into contact with cationic colloids composed of 10 μm in diameter latex particles bearing permanent net positive charge due to their polyethylenimine coating. The determination of the interface (Zeta) potential showed that the wild-type supernatants induced a strong charge inversion of the cationic colloids, indicative of their highly anionic nature as compared to the supernatants of their respective capsule mutants (FIG. 6a). Moreover, the treatment of acid-cleaned glass slides with active supernatant lowered the water-slide interfacial energy, which is indicative of their hydrophilic nature (FIG. 6b).

Figure 6C:
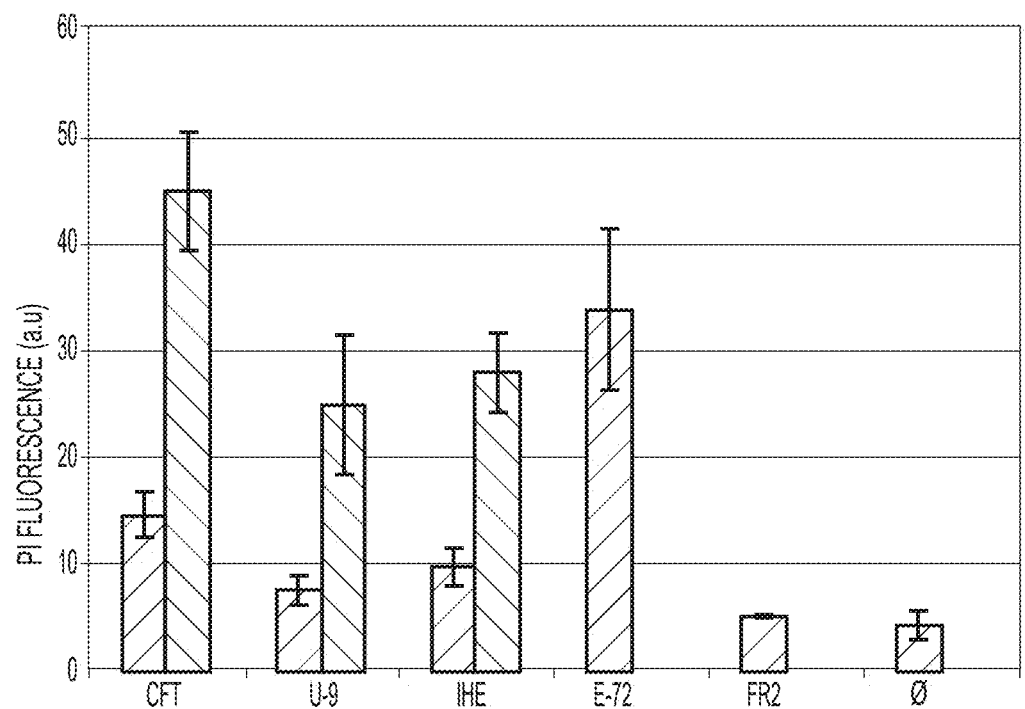
Figure 6D:
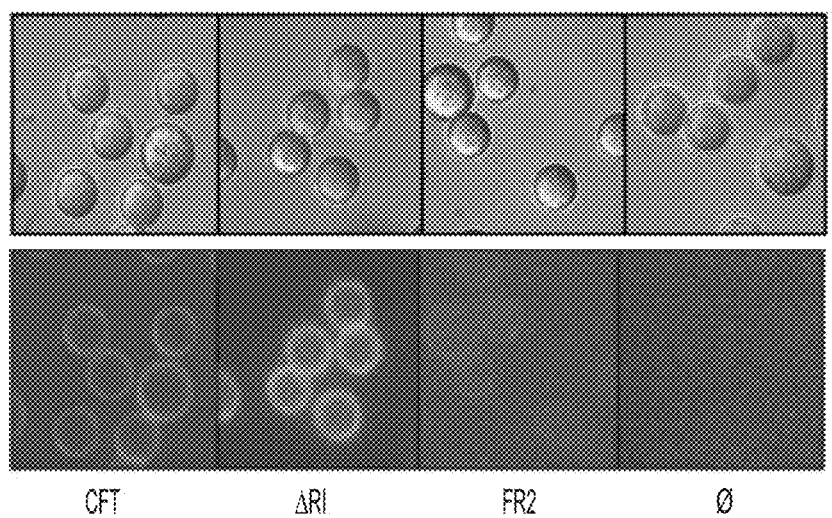

To analyze whether group II capsule could induce surface modifications and affect intermolecular forces on the treated surfaces, the inventors monitored the adsorption of propidium iodide, a fluorescent amphiphillic cationic ion, on colloids coated with active or inactive supernatants. They first showed that anionic but inactive supernatant of the non-group II capsulated *E. coli* EcoR72 displayed strong affinity for the cationic fluorescent probe (FIG. 6c). Despite their high negative charge, active supernatants displayed significantly lower probe affinity than inactive but less negatively charged capsule mutant supernatants (FIGS. 6 *c* and 6*d*). This effect was even more pronounced with the 500 kDa K2 capsular active fraction (FR2) purified from CFT073 by anion exchange-chromatography containing galactose, glycerol, phosphate and acetate in the molar ratio of 1:2:1:1 (Jane et al., 1980) (FIGS. 6*c* and 6*d*). Therefore, these results showed that, besides strong electrostatic modifications, active supernatants also induced a profound remodelling of the colloid surface properties, possibly including surface hydration and steric repulsion. These analyses confirm that the surface modifications induced by group II capsule are more critical for the biofilm inhibition activity than the capsule primary composition.

Example 5

Prevention of Biofilm Development

Figure 2A:
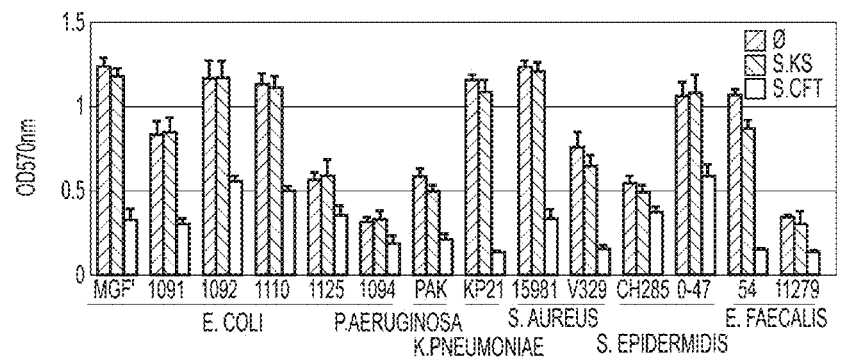
FIGS. 2A to 2D: Effect of CFT073 supernatant on Grampositive and Gram-negative bacterial biofilm formation. A, Quantification of the microtiter plate biofilm formation of different bacteria, alone (θ), with KS272 (S.KS) or CFT073 (S.CFT) supernatant. Levels of crystal violet retained were measured spectrophotometrically ($OD_{570\ nm}$). B, Quantification of biofilm formed by several pathogenic bacteria in microfermentors using media not supplemented (θ), or supplemented with S.CFT or S.KS. Error bars represent standard deviation of two independent experiments. C, Effect of CFT073 supernatant (S.CFT073) in mix biofilms of E. coli (MG1655F') with P. aeruginosa (PAK), K. pneumoniae (KP21), S. epidermidis (0-47), S. aureus (15981) and S. epidermidis (0-47) with S. aureus (15981) and E. faecalis (54). Supernatant of E. coli CFT073ΔkpsD strain (S. ΔkpsD) that do not secrete any group II capsule is used as negative control. D, Qualitative analysis of biofilm formation of S. aureus and P. aeruginosa, in a microfermentor using media not supplemented, or supplemented with CFT073 supernatant.
Figure 2B:
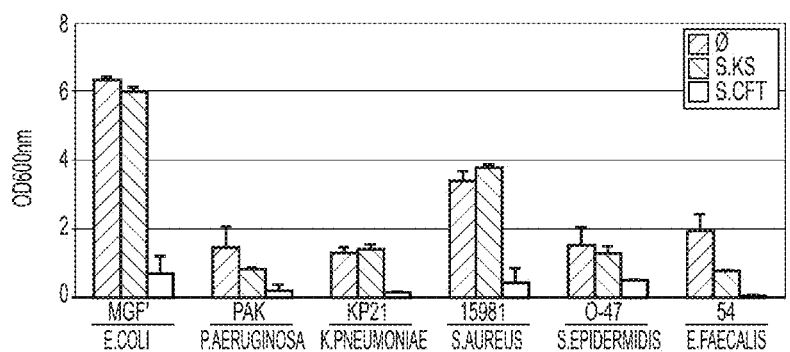
Figure 2C:
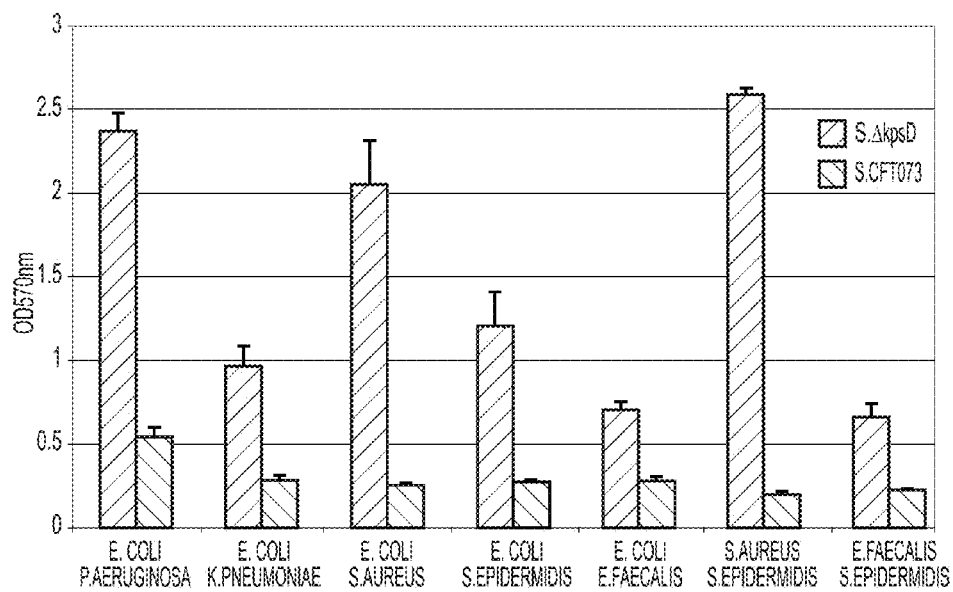
Figure 2D:
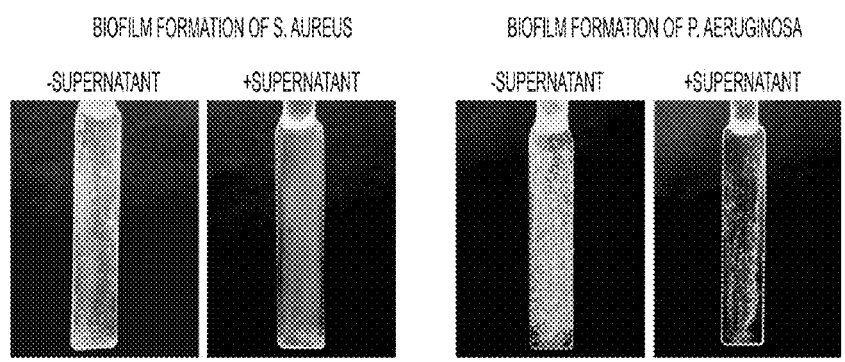
Figure 7:
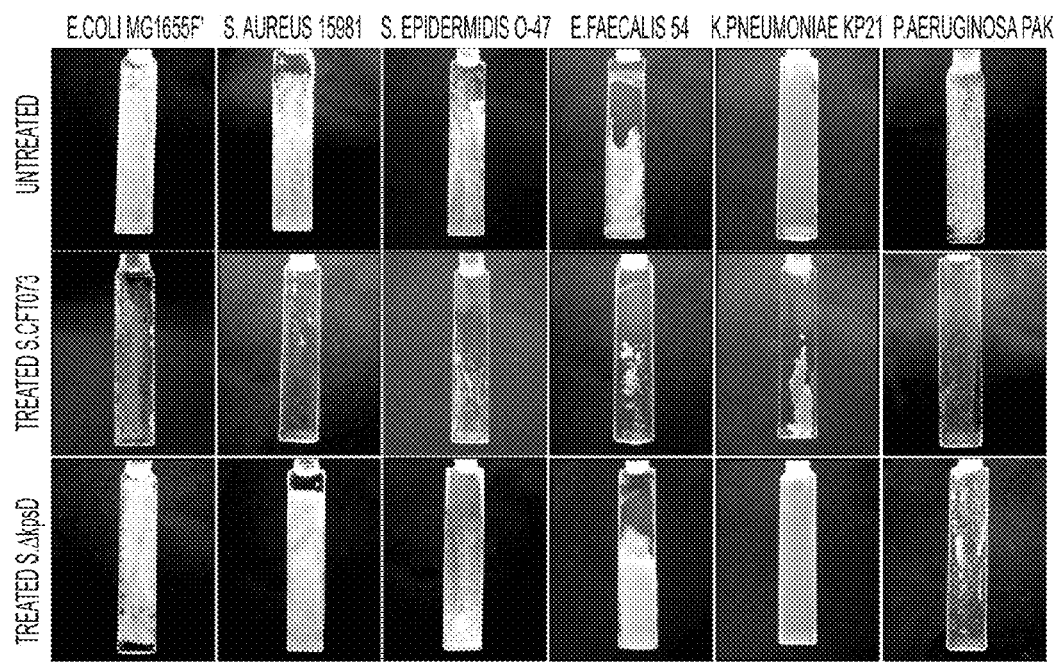
FIG. 7: Biofilm inhibition effect of CFT073 supernatant on coated surfaces. Biofilm formation in microfermentors by several bacteria using: untreated glass slides (upper panel), glass slides treated with CFT073 supernatant (middle panel) and glass slides treated with CFT073ΔkpsD supernatant (lower panel).

The physico-chemical properties displayed by group II capsule might deeply alter bacterial ability to interact with surfaces and therefore drastically reduce adhesion (Neu, 1996). To test this hypothesis, the capacity of both MG1655F' and *S. aureus* to adhere to glass surfaces pre-treated with CFT073 supernatant was analysed. After 1 hour of incubation, *E. coli* MG1655 F' and *S. aureus* 15981 exhibited a 3-fold reduction in their initial adhesion on treated surface (data not shown). Consistently, pre-treatment of the internal microfermentor glass slide with CFT073 supernatant drastically reduced biofilm formation by *E. coli* and a wide range of Gram-positive and Gram-negative bacteria (FIG. 7). The same effect was observed when CFT073 supernatant was perfused in the microfermentor (FIG. 2B). No effect was observed when a similar treatment was performed with CFT073☐kpsD supernatant (FIG. 7). These results therefore suggested that the surface modifications induced by capsular polysaccharides released in the CFT073 supernatant could interfere with biofilm formation by impairing initial bacterial-surface interactions.

Figure 8:
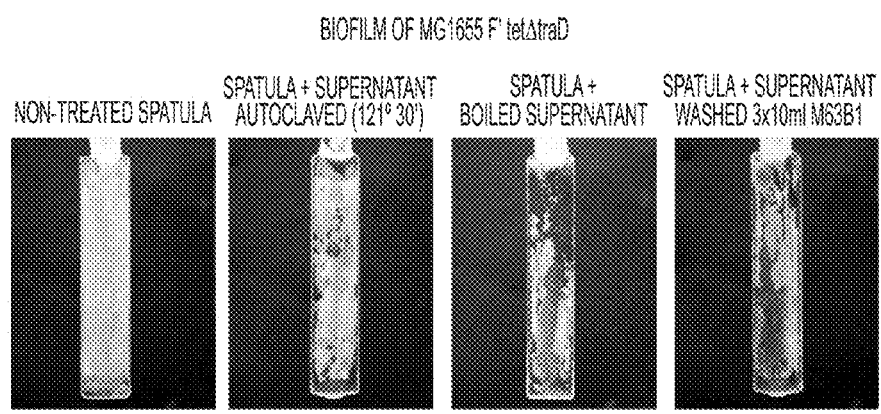
FIG. 8 Impact of the treatment of spatula coated with S.CFT073 supernatant (S.CFT). Biofilm formation in microfermentors by MG1655F' using untreated glass slides and glass slides treated with S.CFT or with boiled S.CFT, and then autoclaved or submitted to intensive wash.

Remarkably, the anti-biofilm effect of the CFT073 supernatant persisted even after drastic treatments of the glass slide (FIG. 8), which suggests that the group II capsule could be used in applications which necessitate a sterilisation step (such as agro-industrial or medical applications).

Figure 9A:
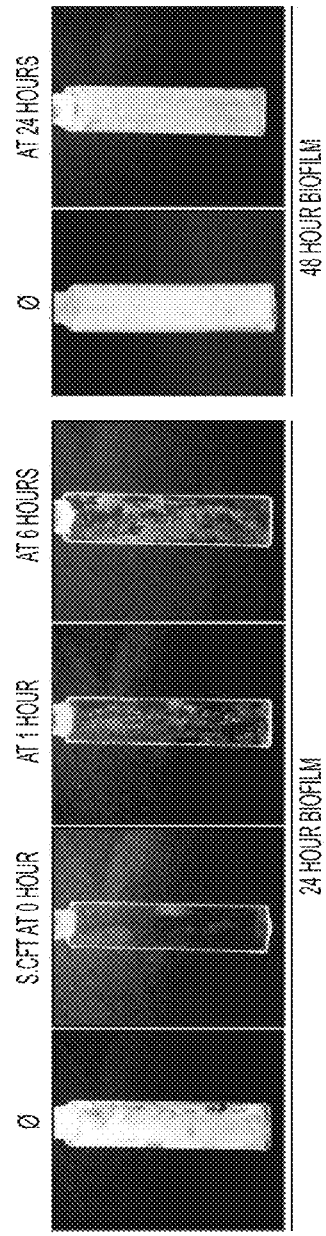
FIG. 9A to 9C CFT073 supernatant affects cell-cell interaction. A, MG1655F' biofilm formation in microfermentors with media supplemented with CFT073 supernatant (S.CFT) at times 0 h, 1 h, 6 h (24 h of culture) and 24 h (48 h of culture). θ: no addition of S.CFT. B, GFP-tagged MG1655F' inoculated in a flow-cell and monitored by confocal microscopy. CFT073 or KS272 supernatants were supplemented after 3 h of culture and biofilms were grown for 12 h total. C, Autoaggregation assay with strains that aggregate via different mechanisms: MG1655F' (F conjugative pilus expression); MG1655ompR234 (curli overexpression); MG1655 ΔoxyR (Ag43 autotransporter adhesin overexpression); 1094 (cellulose production). Cells were diluted to $OD_{600}$ of 2 in 3 ml of M63B1 (triangle), CFT073 supernatant (circle) and ΔkpsD supernatant (rectangle).
Figure 9B:
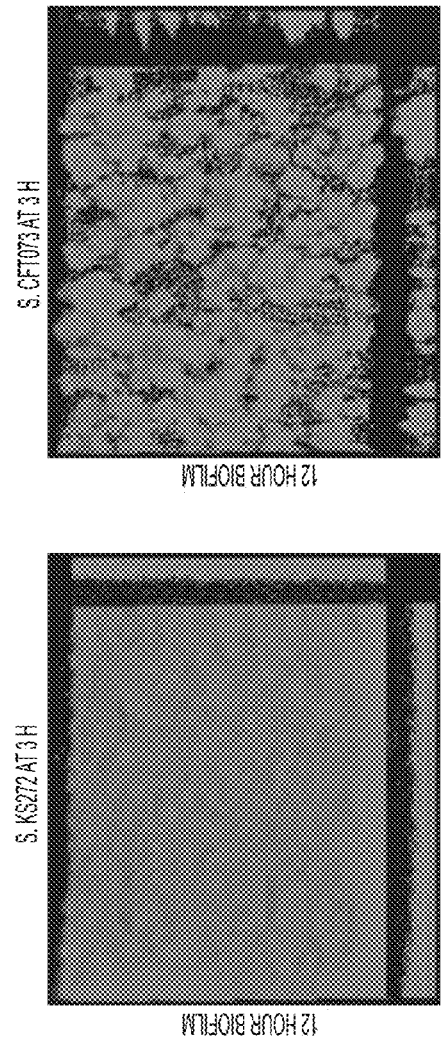

In order to investigate the effect of CFT073 supernatant on already existing biofilms, microfermentors inoculated with MG1655 F' at different stages of biofilm maturation were supplemented with filtered CFT073 supernatant. This analysis showed that, whereas the treatment of a mature 24 h biofilm did not induce biofilm dispersal, addition of the CFT073 supernatant at 0, 1 and 6 h after MG1655 F' biofilm initiation blocked its further development (FIG. 9A). The inventors then examined the in vitro biofilm characteristics of a GFP-tagged MG1655F' after addition of CFT073 supernatant and confocal laser scanning microscopy (CLSM). After 3 h post initial inoculation, the addition of active CFT073 exogenous supernatant on a regularly covered surface profoundly affected MG1655F' mature biofilm structure development (FIG. 9B). This effect was not observed upon control KS272 supernatant treatment.

Figure 9C:
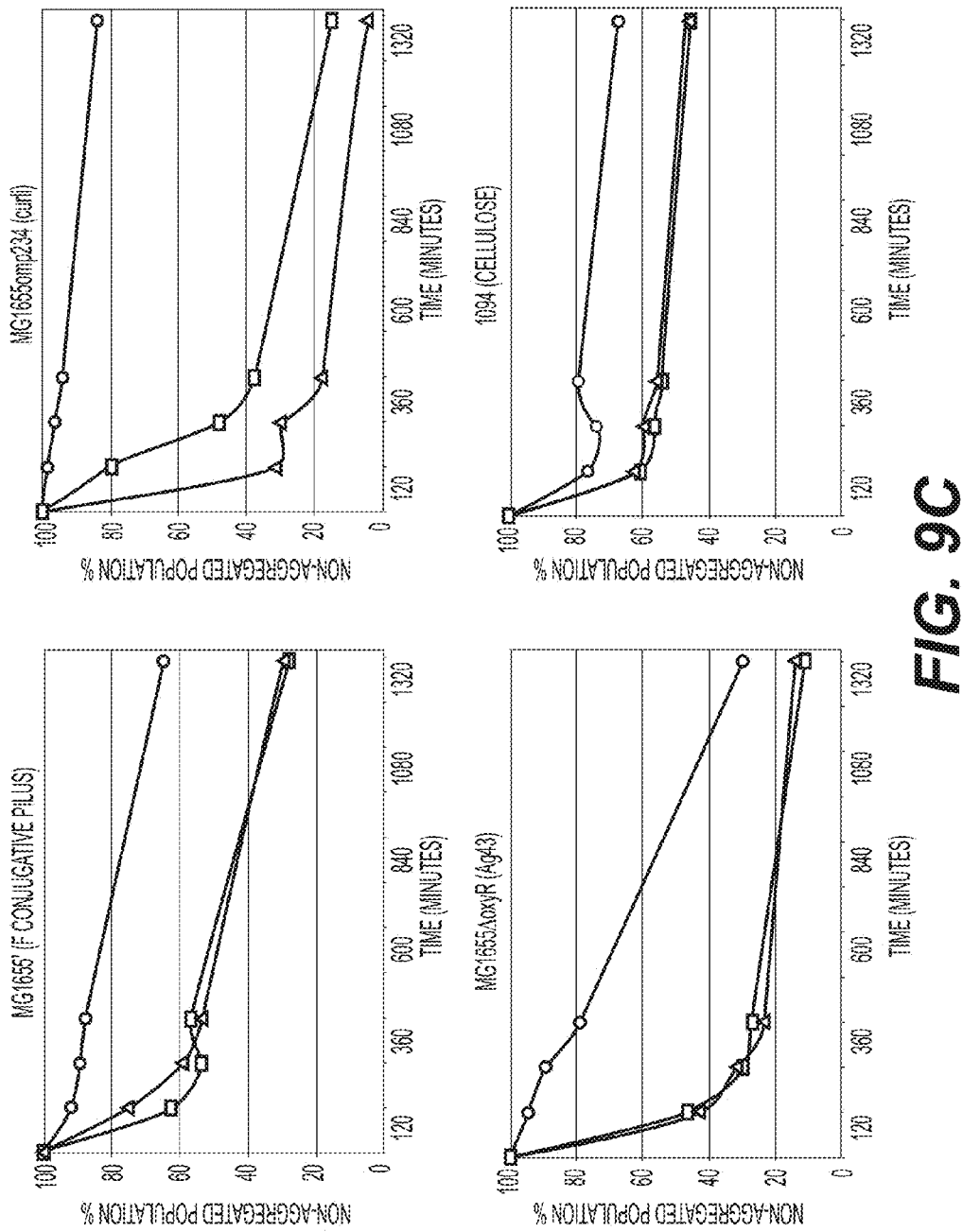

The direct contribution of bacterial surface structures to the tri-dimensional *E. coli* biofilm structure has been amply demonstrated (Beloin et al., 2005). These structures have also been shown to mediate bacterial aggregation and clumping in standing cultures. To further characterize the role of group II capsule in biofilm maturation, the inventors tested its effects on bacterial aggregation mediated by several different surface-exposed factors also involved in biofilm formation. It was shown that CFT073 supernatant prevents formation of bacterial aggregates induced by different types of bacterial surface structures (FIG. 9C).

The anti-biofilm activity of different concentrations of the FR2 fraction was tested in microtiter plate assays. This showed that the purified FR2 fraction is active at concentrations starting from 50 µg/ml (FIG. 10).

Taken together, these results suggest that the physico-chemical properties of the group II capsular polysaccharides affect biofilm formation by weakening cell-surface contacts (initial adhesion) but also by reducing cell-cell interactions (biofilm maturation).

In conclusion, the inventors demonstrated that group II-like capsular polysaccharides are released in the culture supernatant and display anti-adhesion properties against a wide range of bacteria, including important nosocomial pathogens. This study reveals a novel property of the group II capsular polysaccharides that are commonly expressed by extra-intestinal *E. coli*, but also by other pathogens such as *Neisseria meningitides* (Kaijser, 1973; Sandberg et al., 1988), which supernatant could also inhibit *E. coli* biofilm formation (data not shown). Group II capsule has been shown to be involved in UPEC virulence by increasing their resistance to phagocytosis and to the bactericidal effects of human serum (Cross et al., 1986; Kaper et al., 2004; Pluschke et al., 1983; Russo et al., 1995). Capsule could also play an important biological role in UPEC interactions with living and inert surfaces. In particular, besides bacterial competition, the inhibition of UPEC own adhesion by group II capsule secretion may contribute to gastrointestinal tract colonisation by reducing bacteria-bacteria interactions (Schembri et al., 2004), thus avoiding bacterial clearance due to clump formation (Favre-Bonte et al., 1999). Consistently, it was observed that an uncapsulated CFT073□R1 mutant is unable to colonize the mouse intestine (FIG. 11).

The in vitro analyses indicate that group II capsule can induce surface modifications such as charge inversion of cationic surface, increased surface wettability and molecular repulsion, leading to non-specific anti-adhesion properties. Since this inhibitory effect was observed in both exponential and stationary growth phase supernatants as well as in a quorum-sensing □luxS mutant of CFT073 (FIG. 12), this suggests that the anti-biofilm effect does not involve cell-signaling (Waters and Bassler, 2005), but rather acts through physico-chemical alteration, of either abiotic or bacterial surfaces. Polymers assembling on surfaces are known to cause strong physical repulsion depending on their density, size, solvation and structure (de Gennes, 1987). Such repulsive forces created by capsule polymers could limit initial bacterial adhesion and biofilm development by interfering with subsequent cell-cell contacts. Finally, the inventors showed that the application of group II capsular polysaccharides on abiotic surfaces reduces bacterial initial adhesion, and has enough long-lasting effect to significantly inhibit mature biofilm development of a broad-spectrum of bacteria. This finding may have far reaching implications in the design of therapeutic strategies to limit the formation of pathogenic biofilms, for example, on medical implants

REFERENCES

Bahrani-Mougeot, F. K., Buckles, E. L., Lockatell, C. V., Hebel, J. R., Johnson, D. E., Tang, C. M., and Donnenberg, M. S. (2002). Type 1 fimbriae and extracellular polysaccharides are preeminent uropathogenic *Escherichia coli* virulence determinants in the murine urinary tract. Mol Microbiol 45, 1079-1093.

Beloin, C., Da Re, S. & Ghigo, J. M. (2005) in *Escherichia coli* and *Salmonella. Cellular and Molecular Biology*, eds. Curtiss III, R., Bock, A., Ingraham, J. L., Kaper, J. B., Neidhardt, F. C., Riley, M. & Squires, C. L. (ASM Press, Washington, D.C.), pp. Chapter 8.3.1.3.

Beloin, C., Michaelis, K., Lindner, K., Landini, P., Hacker, J., Ghigo, J. M., and Dobrindt, U. (2006). The Transcriptional Antiterminator RfaH Represses Biofilm Formation in *Escherichia coli*. J Bacteriol 188, 1316-1331.

Boyd, E. F., and Hartl, D. L. (1998). Chromosomal regions specific to pathogenic isolates of *Escherichia coli* have a phylogenetically clustered distribution. J Bacteriol 180, 1159-1165.

Caruso, F., Lichtenfeld, H., Donath, E., and Mohwald, H. (1999). Investigation of electrostatic interactions in polyelectrolyte multilayer films: binding of anionic fluorescent probes to layers assembled onto colloids. Macromolecules 32, 2317-2328. Christensen, B. B., Sternberg, C., Andersen, J. B., Palmer, R. J., Jr., Nielsen, A. T., Givskov, M., and Molin, S. (1999). Molecular tools for study of biofilm physiology. Methods Enzymol 310, 20-42.

Cross, A. S., Kim, K. S., Wright, D. C., Sadoff, J. C., and Gemski, P. (1986). Role of lipopolysaccharide and capsule in the serum resistance of bacteremic strains of *Escherichia coli*. J Infect Dis 154, 497-503.

Cucarella, C., Solano, C., Valle, J., Amorena, B., Lasa, I. I., and Penades, J. R. (2001). Bap, a *Staphylococcus aureus* Surface Protein Involved in Biofilm Formation. J Bacteriol 183, 2888-2896.

Da Re, S., and Ghigo, J. M. (2006). A CsgD-independent pathway for cellulose production and biofilm formation in *Escherichia coli*. J Bacteriol 188, in press.

de Gennes, P. G. (1987). Polymers at an interface: a simplified view. Adv Colloid Interface Sci 27, 189-209.

Decher, G. (1997). Fuzzy Nanoassemblies: Toward Layered Polymeric Multicomposites. Science 277, 1232-1237.

Deghmane, A. E., Giorgini, D., Larribe, M., Alonso, J. M., and Taha, M. K. (2002). Down-regulation of pili and capsule of *Neisseria meningitidis* upon contact with epithelial cells is mediated by CrgA regulatory protein. Mol Microbiol 43, 1555-1564. d'Enfert, C., and Fontaine, T. (1997). Molecular characterization of the *Aspergillus nidulans* treA gene encoding an acid trehalase required for growth on trehalose. Mol Microbiol 24, 203-216.

Dubois, M., Gilles, K. A., Hamilton, J. K., Rebers, P. A., and Smith, F. (1956). Colorimetric method for determination of sugars and related substances. Anal Chem 28, 350-356.

Favre-Bonte, S., Licht, T. R., Forestier, C., and Krogfelt, K. A. (1999). *Klebsiella pneumoniae* capsule expression is necessary for colonization of large intestines of streptomycin-treated mice. Infect Immun 67, 6152-6156.

Fontaine, T., Simenel, C., Dubreucq, G., Adam, O., Delepierre, M., Lemoine, J., Vorgias, C. E., Diaquin, M., and Latge, J. P. (2000). Molecular organization of the alkali-insoluble fraction of *aspergillus fumigatus* cell wall. J Biol Chem 275, 41528.

Galdbart, J. O., Allignet, J., Tung, H. S., Ryden, C., and El Solh, N. (2000). Screening for *Staphylococcus epidermidis* markers discriminating between skin-flora strains and those responsible for infections of joint prostheses. J Infect Dis 182, 351-355.

Ghigo, J. M. (2001). Natural conjugative plasmids induce bacterial biofilm development. Nature 412, 442-445.

Hall-Stoodley, L., Costerton, J. W., and Stoodley, P. (2004). Bacterial biofilms: from the natural environment to infectious diseases. Nat Rev Microbiol 2, 95-108.

Heilmann, C., Gerke, C., Perdreau-Remington, F., and Gotz, F. (1996). Characterization of Tn917 insertion mutants of *Staphylococcus epidermidis* affected in biofilm formation. Infect Immun 64, 277-282.

Jann, K., Jann, B., Schmidt, M. A., and Vann, W. F. (1980). Structure of the *Escherichia coli* K2 capsular antigen, a teichoic acid-like polymer. J Bacteriol 143, 1108-1115.

Johnson, J. R., and O'Bryan, T. T. (2004). Detection of the *Escherichia coli* group 2 polysaccharide capsule synthesis Gene kpsM by a rapid and specific PCR-based assay. J Cl in Microbiol 42, 1773-1776.

Kaijser, B. (1973). Immunology of *Escherichia coli*: K antigen and its relation to urinary-tract infection. J Infect Dis 127, 670-677.

Kaper, J. B., Nataro, J. P., and Mobley, H. L. (2004). Pathogenic *Escherichia coli*. Nat Rev Microbiol 2, 123-140.

Leboeuf, D., and Henry, N. (2006). Molecular bond formation between surfaces: anchoring and shearing effects. Langmuir 22, 127-133.

Maroncle, N., Rich, C., and Forestier, C. (2006). The role of *Klebsiella pneumoniae* urease in intestinal colonization and resistance to gastrointestinal stress. Res Microbiol 157, 184-193.

Meier, C., Oelschlaeger, T. A., Merkert, H., Korhonen, T. K., and Hacker, J. (1996). Ability of *Escherichia coli* isolates that cause meningitis in newborns to invade epithelial and endothelial cells. Infect Immun 64, 2391-2399.

Mobley, H. L., Green, D. M., Trifillis, A. L., Johnson, D. E., Chippendale, G. R., Lockatell, C. V., Jones, B. D., and Warren, J. W. (1990). Pyelonephritogenic *Escherichia coli* and killing of cultured human renal proximal tubular epithelial cells: role of hemolysin in some strains. Infect Immun 58, 1281-1289.

Neu, T. R. (1996). Significance of bacterial surface-active compounds in interaction of bacteria with interfaces. Microbiol. Rev 60, 151-166.

Ochman, H., and Selander, R. K. (1984). Standard reference strains of *Escherichia coli* from natural populations. J Bacteriol 157, 690-693.

O'Toole, G. A., and Kolter, R. (1998). Initiation of biofilm formation in *Pseudomonas fluorescens* WCS365 proceeds via multiple, convergent signalling pathways: a genetic analysis. Mol Microbiol 28, 449-461.

Pluschke, G., Mayden, J., Achtman, M., and Levine, R. P. (1983). Role of the capsule and the O antigen in resistance of O18:K1 *Escherichia coli* to complement-mediated killing. Infect Immun 42, 907-913.

Roberts, I. S. (1996). The biochemistry and genetics of capsular polysaccharide production in bacteria. Annu Rev Microbiol 50, 285-315.

Russo, T. A., Sharma, G., Weiss, J., and Brown, C. (1995). The construction and characterization of colanic acid deficient mutants in an extraintestinal isolate of *Escherichia coli* (O4/K54/H5). Microb Pathog 18, 269-278.

Sandberg, T., Kaijser, B., Lidin-Janson, G., Lincoln, K., Orskov, F., Orskov, I., Stokland, E., and Svanborg-Eden, C. (1988). Virulence of *Escherichia coli* in relation to host factors in women with symptomatic urinary tract infection. J Clin Microbiol 26, 1471-1476.

Schachter, B. (2003). Slimy business—the biotechnology of biofilms. Nat Biotechnol 21, 361-365.

Schembri, M. A., Dalsgaard, D., and Klemm, P. (2004). Capsule shields the function of short bacterial adhesins. J Bacteriol 186, 1249-1257.

Silver, R. P., and Vimr, E. R. (1984). Polysialic acid capsule of *Escherichia coli* $K_1$. In Molecular Basis of Bacterial Pathogenesis (Academic Press, Inc., New York), pp. 39-60.

Strauch, K. L., and Beckwith, J. (1988). An *Escherichia coli* mutation preventing degradation of abnormal periplasmic proteins. Proc Natl Acad Sci USA 85, 1576-1580.

Toledo-Arana, A., Valle, J., Solano, C., Arrizubieta, M. J., Cucarella, C., Lamata, M., Amorena, B., Leiva, J., Penades, J. R., and Lasa, I. (2001). The Enterococcal Surface Protein, Esp, Is Involved in *Enterococcus faecalis* Biofilm Formation. Appl Environ Microbiol 67, 4538-4545.

Valle, J., Toledo-Arana, A., Berasain, C., Ghigo, J. M., Amorena, B., Penades, J. R., and Lasa, I. (2003). SarA and not sigmaB is essential for biofilm development by *Staphylococcus aureus*. Mol Microbiol 48, 1075-1087.

Vasseur, P., Vallet-Gely, I., Soscia, C., Genin, S., and Filloux, A. (2005). The pel genes of the *Pseudomonas aeruginosa* PAK strain are involved at early and late stages of biofilm formation. Microbiology 151, 985-997.

Vidal, O., Longin, R., Prigent-Combaret, C., Dorel, C., Hooreman, M., and Lejeune, P. (1998). Isolation of an *Escherichia coli* K-12 mutant strain able to form biofilms on inert surfaces: involvement of a new ompR allele that increases curli expression. J Bacteriol 180, 2442-2449.

Waters, C. M., and Bassler, B. L. (2005). Quorum sensing: cell-to-cell communication in bacteria. Annu Rev Cell Dev Biol 21, 319-346.

Whitfield, C. (2006). Biosynthesis and assembly of capsular polysaccharides in *Escherichia coli*. Annu Rev Biochem 75, 39-68.

Whitfield, C., and Roberts, I. S. (1999). Structure, assembly and regulation of expression of capsules in *Escherichia coli*. Mol Microbiol 31, 1307-1319.

The invention claimed is:

1. A method of inhibiting bacterial adhesion and/or bacterial biofilm development on a medical or industrial device, comprising
coating a surface of the device with a sufficient amount of a composition comprising a mixture of soluble group II capsular polysaccharides isolated from a cell-free supernatant of a culture of a bacterial strain comprising a group II capsule, wherein the mixture is in an amount effective to inhibit bacterial adhesion and/or bacterial biofilm development on the surface.

2. The method of claim 1, wherein the bacterial strain is a strain of a bacteria selected from the group consisting of *E. coli, H influenzae* and *N. meningitidis*.

3. The method of claim 1, wherein the surface of the device is dip coated with the composition.

4. The method of claim 1, wherein the composition is applied to the surface of the device as a sheet.

5. The method of claim 1, wherein the surface of the device is painted with the composition.

6. The method of claim 1, wherein the surface-coated device is heat sterilized.

7. The method of claim 1, wherein the device is an industrial device.

8. The method of claim 7, wherein the industrial device is a pipe, tube, or valve.

9. The method of claim 7, wherein the industrial device is an air-cooled tower, warm water system, coolant circuit, silo, fermenter, colander, or furniture element.

10. The method of claim 1, wherein the device is a medical device.

11. The method of claim 10, wherein the medical device is a non-disposable dental tool.

12. The method of claim 10, wherein the medical device is a non-disposable surgical tool.

13. The method of claim 10, wherein the medical device is an indwelling implant.

14. The method of claim 13, wherein the medical device is a dental implant.

15. The method of claim 13, wherein the medical device is a catheter.

16. The method of claim 13, wherein the medical device is cardiac implant.

17. The method of claim 13, wherein the medical device is a stent.

18. The method of claim 10, wherein the medical device is ventilator tubing.

* * * * *

SEQUENCE LISTING

```
<160> NUMBER OF SEQ ID NOS: 92

<210> SEQ ID NO 1
<211> LENGTH: 24
<212> TYPE: DNA
<213> ORGANISM: Artificial Sequence
```

```
-continued

<220> FEATURE:
<223> OTHER INFORMATION: Description of Artificial Sequence: Synthetic
      oligonucleotide
<220> FEATURE:
<223> OTHER INFORMATION: KpsD.500-5

<400> SEQUENCE: 1
gaccagcttg cctttgcaga aacg                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.500-3

<400> SEQUENCE: 2 cttttttcagc attacgcgga tagg                                           24

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.GB.L-5

<400> SEQUENCE: 3
tgctcgatga gttttctaa ggagttgaaa tgagcaa                               37

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.GB.L-3

<400> SEQUENCE: 4
gattttgaga cacaacgtgg ctttcatcac aaactcattc agcgaca                   47

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.ext-5

<400> SEQUENCE: 5
ttgcgcttaa gtttaaccaa accg                                            24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: KpsD.ext-3

<400> SEQUENCE: 6
gctctggcat ggactccggt aact                                      24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsU.500-5

<400> SEQUENCE: 7
atgaacgcag ttcagcttta tcgcc                                     25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsU.500-3

<400> SEQUENCE: 8
ccaaatttcg gcttgaggat tttc                                      24

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsU.GB.L-5

<400> SEQUENCE: 9
tgctcgatga gttttctaa caggaactgg ctgaaaacgc atga                 44

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsU.GB.L-3

<400> SEQUENCE: 10
gattttgaga cacaacgtgg ctttcatttc aactccttac aaagacaga           49

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsU.ext-5

<400> SEQUENCE: 11
tgcagaacgg cgatacctta atcg                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsU.ext-3

<400> SEQUENCE: 12
ctcggcaatc aaacgtactc gttg                                          24

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsC.500-5

<400> SEQUENCE: 13
gaggcagata tcaacattaa cc                                            22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsC.500-3

<400> SEQUENCE: 14
gttgaaggtt ttaagttctc aac                                           23

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsC.GB.L-5

<400> SEQUENCE: 15
tgctcgatga gtttttctaa acaatttcat agttgactat tac                     43

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsC.GB.L-3

<400> SEQUENCE: 16
gattttgaga cacaacgtgg ctttgagtaa atgccaatca tgcgttttc               49

<210> SEQ ID NO 17

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsC.ext-5

<400> SEQUENCE: 17
cgactcacat tacgattatg cg                                              22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsC.ext-3

<400> SEQUENCE: 18
gaaaatgatt tgtggtggcg gtagc                                           25

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.500-5

<400> SEQUENCE: 19
agagcaacct tgagttatta cg                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.500-3

<400> SEQUENCE: 20
aaagacaagg gatagcttta gg                                              22

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.GB.L-5

<400> SEQUENCE: 21
tgctcgatga gtttttctaa tttattctaa attatcaacg                           40

<210> SEQ ID NO 22
<211> LENGTH: 49
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: KpsS.GB.L-3

<400> SEQUENCE: 22
gattttgaga cacaacgtgg ctttcataaa taatctgtgt aatagtcaa        49

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.ext-5

<400> SEQUENCE: 23
agcgactggt tgaaagcaaa ctg                                    23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.ext-3

<400> SEQUENCE: 24
ttcgatgagt caagactatt gg                                     22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.500-5

<400> SEQUENCE: 25
ttactacgca taaaattcat gg                                     22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.500-3

<400> SEQUENCE: 26
aatgccatgc ttaaaccaaa gcc                                    23

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.GB.L-5
```

<400> SEQUENCE: 27
tgctcgatga gttttctaa caatgctgac atcatgatta agattg          46

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.GB.L-3

<400> SEQUENCE: 28
gattttgaga cacaacgtgg ctttcttgcc atttggtgat gtgatcct          48

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.ext-5

<400> SEQUENCE: 29
tcgcatgcgt tctggtttga g          21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.ext-3

<400> SEQUENCE: 30
cacatcacaa aactctttca atg          23

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.500-5

<400> SEQUENCE: 31
gaccagcttg cctttgcaga aacg          24

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.500-3

<400> SEQUENCE: 32
aaagacaagg gatagcttta gg          22

```
<210> SEQ ID NO 33
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.GB.L-3

<400> SEQUENCE: 33
gattttgaga cacaacgtgg ctttcatcac aaactcattc agcgaca            47

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.GB.L-3

<400> SEQUENCE: 34
gattttgaga cacaacgtgg ctttcataaa taatctgtgt aatagtcaa          49

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsD.ext-5

<400> SEQUENCE: 35
ttgcgcttaa gtttaaccaa accg                                     24

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsS.ext-3

<400> SEQUENCE: 36
ttcgatgagt caagactatt gg                                       22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR2.500-5

<400> SEQUENCE: 37
atataggagt atggagcgaa ac                                       22

<210> SEQ ID NO 38
<211> LENGTH: 22
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR2.500-3

<400> SEQUENCE: 38
ttgagtaagg aatatggctt ag                                              22

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR2.GB-L5

<400> SEQUENCE: 39
tgctcgatga gttttttctaa gaaatcagac gagttttc                            38

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR2.GB-L3

<400> SEQUENCE: 40
gattttgaga cacaacgtgg ctttcataac atactatgtc cccatgatta tt             52

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR2.ext-5

<400> SEQUENCE: 41
catgtactca ttttcacgta aag                                             23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR2.ext-3

<400> SEQUENCE: 42
tgctaaaatt gcattattag gtc                                             23

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: KpsM.500-5

<400> SEQUENCE: 43
ttactacgca taaaattcat gg                                          22

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR3.500-3

<400> SEQUENCE: 44
aattaaccat atcttttgat ttgag                                       25

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR3.GB-L5

<400> SEQUENCE: 45
tgctcgatga gttttctaa atcagacttg tctttatcag                        40

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.GB.L-3

<400> SEQUENCE: 46
gattttgaga cacaacgtgg ctttcttgcc atttggtgat gtgatcct              48

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsM.ext-5

<400> SEQUENCE: 47
tcgcatgcgt tctggtttga g                                           21

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsR3.ext-3

```
<400> SEQUENCE: 48
cctagcaaca aaatatttag cgac                                          24

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps95-96.500-5

<400> SEQUENCE: 49
aaacaatatc atggccagtc gg                                            22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps95-96.500-3

<400> SEQUENCE: 50
aataacgttc aggtattgaa gg                                            22

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps95-96.GB-L5

<400> SEQUENCE: 51
tgctcgatga gttttctaa ccttgaggtc tatataactg aa                       42

<210> SEQ ID NO 52
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps95-96.GB-L3

<400> SEQUENCE: 52
gattttgaga cacaacgtgg ctttcatcaa atgtaccaaa ggtgataac               49

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps95-96.ext-5

<400> SEQUENCE: 53
taaatcaacg ttactgagaa tg                                            22
```

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Kps95-96.ext-3

<400> SEQUENCE: 54
gaatatccga gtgcataata cc                                              22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Kps95-96.500-5

<400> SEQUENCE: 55
aaacaatatc atggccagtc gg                                              22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: c3694.500-5

<400> SEQUENCE: 56
aagcattaga attggaaccc                                                 20

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: c3694.500-3

<400> SEQUENCE: 57
ctttccatgt attcctctcc aag                                             23

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: c3694.GB.L-5

<400> SEQUENCE: 58
tgctcgatga gtttttctaa gtgcaagtat ttcttgtaac cc                        42

<210> SEQ ID NO 59
<211> LENGTH: 50
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3694.GB.L-3

<400> SEQUENCE: 59
gattttgaga cacaacgtgg ctttcatata cgcatcaata gccttagccc            50

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3694.ext-5

<400> SEQUENCE: 60
gcggagagct attttaaagc agg                                        23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3694.ext-3

<400> SEQUENCE: 61
cggaaaacga tatgacaatc ctg                                        23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3693.500-5

<400> SEQUENCE: 62
gtttattgtt gcaggcatcc aag                                        23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3693.500-3

<400> SEQUENCE: 63
atgccgttag atagttttat tcc                                        23

<210> SEQ ID NO 64
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: c3693.GB.L-5

<400> SEQUENCE: 64
tgctcgatga gttttctaa atggatgctc aaaaggaggt acg        43

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3693.GB.L-3

<400> SEQUENCE: 65
gattttgaga cacaacgtgg ctttcatcag cattggttgg taatgcattt g        51

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3693.ext-5

<400> SEQUENCE: 66
acatattaac agtaatataa cc        22

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3693.ext-3

<400> SEQUENCE: 67
ctacaaattt ggatactgca aatc        24

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3692.500-5

<400> SEQUENCE: 68
ttatacttgc ggtgatttgc ag        22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3692.500-3

<400> SEQUENCE: 69
atgactcata aaatatatt cc                                           22

<210> SEQ ID NO 70
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3692.GB.L-5

<400> SEQUENCE: 70
tgctcgatga gttttctaa tatttacaga ataattattc tgg                    43

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3692.GB.L-3

<400> SEQUENCE: 71
gattttgaga cacaacgtgg ctttcattaa gccaatagtc ttgactcatc g           51

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3692.ext-5

<400> SEQUENCE: 72
aattcatatg attgtagcaa tg                                          22

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: c3692.ext-3

<400> SEQUENCE: 73
caacgtagaa taaaagcatt acc                                         23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LuxS.500-5

<400> SEQUENCE: 74
aaactgcgca gttcccgtta cc                                          22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: LuxS.500-3

<400> SEQUENCE: 75
cctgattttg ttccctggga gg                                             22

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: LuxS.GB-L5

<400> SEQUENCE: 76
tgctcgatga gttttctaa tcagtggaac aaaagaag                             38

<210> SEQ ID NO 77
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: LuxS.GB-L3

<400> SEQUENCE: 77
gattttgaga cacaacgtgg ctttcattta gccacctccg gtaattt                  47

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: LuxS.ext-5

<400> SEQUENCE: 78
ctggaaccgg gtgatcctcg aag                                            23

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: LuxS.ext-3

<400> SEQUENCE: 79
agcaacaatg ctggggaaaa atgc                                           24

<210> SEQ ID NO 80
<211> LENGTH: 22
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Kps95-F

<400> SEQUENCE: 80
aacgaaaatt gcttgctctg gc                                            22

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps94-R

<400> SEQUENCE: 81
cggtgccaag tttgaaataa cg                                            22

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps94-F

<400> SEQUENCE: 82
gaaaatagtg tagacggtct cttc                                          24

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kps92-R

<400> SEQUENCE: 83
tttggatact gcaaatcacc gc                                            22

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KpsIIf

<400> SEQUENCE: 84
gcgcatttgc tgatactgtt g                                             21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: KpsK2r

<400> SEQUENCE: 85
aggtagttca gactcacacc t                                               21

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KmGB.verif-5

<400> SEQUENCE: 86
tggctccctc actttctggc                                                 20

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: KmGB.verif-3

<400> SEQUENCE: 87
atatggctca taacacccct tg                                              22

<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ARB1
<220> FEATURE:
<221> NAME/KEY: modified_base
<222> LOCATION: (21)..(30)
<223> OTHER INFORMATION: a, c, t, or g

<400> SEQUENCE: 88
ggccacgcgt cgactagtac nnnnnnnnnn gatat                                35

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ARB6
<220> FEATURE:
<221> NAME/KEY: modified_base
<222> LOCATION: (21)..(30)
<223> OTHER INFORMATION: a, c, t, or g

<400> SEQUENCE: 89
ggccacgcgt cgactagtac nnnnnnnnnn acgcc                                35

<210> SEQ ID NO 90
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: ARB2

<400> SEQUENCE: 90
ggccacgcgt cgactagtac                                                    20

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: IR2

<400> SEQUENCE: 91
ctgaccgctt cctcgtgctt tacgg                                              25

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: IR2-60-5

<400> SEQUENCE: 92
ttctgagcgg gactctgggg tacg                                               24
```